United States Patent
Gajewski et al.

(10) Patent No.: US 7,468,449 B2
(45) Date of Patent: Dec. 23, 2008

(54) PHENYL-FURAN COMPOUNDS AS VITAMIN D RECEPTOR MODULATORS

(75) Inventors: Robert Peter Gajewski, Indianapolis, IN (US); Charles David Jones, Indianapolis, IN (US); Jianliang Lu, Fishers, IN (US); Tianwei Ma, Carmel, IN (US); Sunil Nagpal, Carmel, IN (US); Ying Kwong Yee, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 169 days.

(21) Appl. No.: 10/578,991

(22) PCT Filed: Nov. 16, 2004

(86) PCT No.: PCT/US2004/035527

§ 371 (c)(1),
(2), (4) Date: May 11, 2006

(87) PCT Pub. No.: WO2005/051936

PCT Pub. Date: Jun. 9, 2005

(65) Prior Publication Data

US 2007/0105951 A1    May 10, 2007

Related U.S. Application Data

(60) Provisional application No. 60/524,015, filed on Nov. 20, 2003.

(51) Int. Cl.
C07D 307/02    (2006.01)
A61K 31/34     (2006.01)

(52) U.S. Cl. ........................... 549/487; 514/471

(58) Field of Classification Search ............... 549/498, 549/486, 487; 514/471
See application file for complete search history.

(56) References Cited

U.S. PATENT DOCUMENTS 4,282,246 A * 8/1981 Holland ............... 514/446

| | | |
|---|---|---|
| 6,218,430 B1 | 4/2001 | Allegretto et al. |
| 2006/0094778 A1 | 5/2006 | Nagpal et al. |
| 2006/0135484 A1 | 6/2006 | Nagpal et al |
| 2006/0287536 A1 | 12/2006 | Dahnke et al. |
| 2006/0293385 A1 | 12/2006 | Gajewski et al. |
| 2007/0105951 A1 | 5/2007 | Gajewski et al. |
| 2007/0106095 A1 | 5/2007 | Lu et al. |
| 2007/0149810 A1 | 6/2007 | Lu et al. |

FOREIGN PATENT DOCUMENTS

WO    WO 2005/051893    6/2005

OTHER PUBLICATIONS

Masahiko Inouye, Toshiyuki Miyake, Masaru Furusyo, Hiroyuki Nakazumi: "Molecular recognition of beta-Ribofuranosides by synthetic polypyridine_macrocyclic receptors" J.Am. Chem. Soc. vol. 117, 1995, pp. 12416-12425, XP001206518.
Ping Huang, John Ramphal, James Wei, Congxin Liang, Bahija Jallal, Gerald McMahon and Cho Tang: "Structure-based design and discovery of novel inhibitors of protein tyrosine phosphatases" Bioorganic & Medicinal Chemistry, vol. 11, 2003, pp. 1835-1849, XP001206517.
Boehm, M., "Novel Nonsecosteroidal Vitamin D Mimics Exert VDR-modulating Activities" *Chemistry & Biology*, 1999, 265-275, vol. 6(5).
Nagpal, S. et al. "Vitamin D Analogs: Mechanism of Action of Therapeutic Applications", *Curr. Med. Chem.* 2001, 1661-1679, vol. 8.
Bouillon R., et al. Endocrine Rev. 1995, 200-257, vol. 16.
Swann et al. "Rational Design of Vitamin D3 Analogues Which Selectively Restore Activity to a Vitamin D Receptor Mutant Associated with Rickets" *Org. Lett.* 2002, p. 1863-3866 vol. 4.
Swann et al. "Structure-Based Design of Selective Agonists for a Rickets-Associated Mutant of the Vitamin D Receptor" *J. Am. Chem. Soc.* 2002 13795-13805, vol. 124.

* cited by examiner

*Primary Examiner*—D. Margaret Seaman
*Assistant Examiner*—Nizal S Chandrakumar
(74) *Attorney, Agent, or Firm*—James B. Myers

(57) ABSTRACT

The present invention relates to novel, non-secosteroidal, phenyl-furan compounds with vitamin D receptor (VDR) modulating activity that are less hypercalcemic than 1α,25dihydroxy vitamin D3. These compounds are useful for treating bone disease and psoriasis.

9 Claims, No Drawings

PHENYL-FURAN COMPOUNDS AS VITAMIN D RECEPTOR MODULATORS

This application is submitted as a United States national phase entry, pursuant to 35 U.S.C. §371, of PCT/US2004/035527, filed on 16 Nov. 2004, which claims the benefit of U.S. provisional patent application serial No. 60/524,015, filed 20 Nov. 2003, which is incorporated by reference herein.

BACKGROUND OF THE INVENTION

Vitamin $D_3$ Receptor (VDR) is a ligand dependent transcription factor that belongs to the superfamily of nuclear hormone receptors. The VDR protein is 427 amino acids, with a molecular weight of ~50 kDa. The VDR ligand, 1α,25-dihydroxyvitamin D3 (the hormonally active form of Vitamin D) has its action mediated by its interaction with the nuclear receptor known as Vitamin D receptor ("VDR"). The VDR ligand, 1α,25-dihydroxyvitamin D3 (1α,25(OH)$_2$D$_3$) acts upon a wide variety of tissues and cells both related to and unrelated to calcium and phosphate homeostasis.

The activity of 1α,25-dihydroxyvitamin D3 (1α,25(OH)$_2$D$_3$) in various systems suggests wide clinical applications. However, use of conventional VDR ligands is hampered by their associated toxicity, namely hypercalcemia (elevated serum calcium). Currently, 1α,25(OH)$_2$D$_3$, marketed as Rocaltrol® pharmaceutical agent (product of Hoffmann-La Roche), is administered to kidney failure patients undergoing chronic kidney dialysis to treat hypocalcemia and the resultant metabolic bone disease. Other therapeutic agents, such as Calcipotriol® (synthetic analog of 1α,25(OH)$_2$D$_3$) show increased separation of binding affinity on VDR from hypercalcemic activity.

Recently, chemical modifications of 1α,25(OH)$_2$D$_3$ have yielded analogs with attenuated calcium mobilization effects (R. Bouillon et. al., Endocrine Rev. 1995, 16, 200-257). One such analog, Dovonex® pharmaceutical agent (product of Bristol-Meyers Squibb Co.), is currently used in Europe and the United States as a topical treatment for mild to moderate psoriasis (K. Kragballe et. al., Br. J. Dermatol. 1988, 119, 223-230).

Other vitamin $D_3$ mimics have been described in the publication, *Vitamin D Analogs: Mechanism of Action of Therapeutic Applications*, by Nagpal, S.; Lu, J.; Boehm, M. F., Curr. Med. Chem. 2001, 8, 1661-1679.

Although some degree of separation between the beneficial action and calcium raising (calcemic) effects has been achieved with these VDR ligands, to date the separation has been insufficient to allow for oral administration to treat conditions such as osteoporosis, cancers, leukemias, and severe psoriasis.

One example of a major class of disorder that could benefit from VDR mediated biological efficacy in the absence of hypercalcemia is osteoporosis. Osteoporosis is a systemic disorder characterized by decreased bone mass and microarchitectural deterioration of bone tissue leading to bone fragility and increased susceptibility to fractures of the hip, spine, and wrist (World Health Organization WHO 1994). Osteoporosis affects an estimated 75 million people in the United States, Europe, and Japan.

Within the past few years, several antiresorptive therapies have been introduced. These include bisphosphonates, hormone replacement therapy (HRT), a selective estrogen receptor modulator (SERM), and calcitonins. These treatments reduce bone resorption, bone formation, and increase bone density. However, none of these treatments increase true bone volume nor can they restore lost bone architecture.

Synthetic vitamin D receptor (VDR) ligands with reduced calcemic potential have been synthesized. For example, a class of bis-phenyl compounds stated to mimic 1α,25-dihydroxyvitamin $D_3$ is described in U.S. Pat. No. 6,218,430 and the article; "Novel nonsecosteroidal vitamin D mimics exert VDR-modulating activities with less calcium mobilization than 1α,25-Dihydroxyvitamin $D_3$," by Marcus F. Boehm, et. al., *Chemistry & Biology* 1999, Vol 6, No. 5, pgs. 265-275.

There remains a need for improved treatments using alternative or improved pharmaceutical agents that mimic 1α,25-dihydroxyvitamin $D_3$ to stimulate bone formation, restore bone quality, and treat other diseases without the attendant disadvantage of hypercalcemia.

SUMMARY OF THE INVENTION

Novel compounds having a nucleus of formula "(A)" have been found effective as Vitamin D Receptor (VDR) modulators:

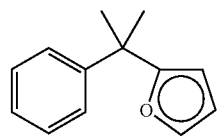

(A)

Compounds of the present invention with VDR modulating activities are represented by formula (I)

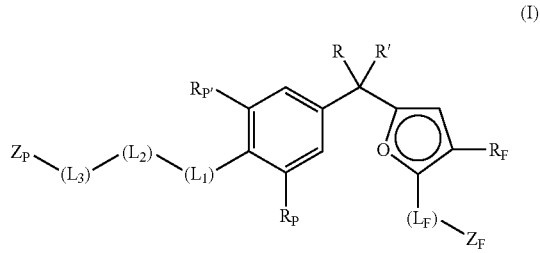

(I)

wherein the variables R, R', $R_P$, $R_{P'}$, $L_1$, $L_2$, $L_3$, $Z_P$, $R_F$, $L_F$, and $Z_F$, and are as hereinafter defined. The inventors have discovered that compounds described herein display the desirable cell differentiation and antiproliferative effects of 1,25(OH)$_2$D$_3$ with reduced calcium mobilization (calcemic) effects.

In another aspect, the present invention is directed towards pharmaceutical compositions containing pharmaceutically effective amounts of compounds of formulae I or a pharmaceutically acceptable salt or prodrug thereof, either singly or in combination, together with pharmaceutically acceptable carriers and/or auxiliary agents.

Another aspect of the invention are novel chemical intermediates suitable for preparing the compounds of Formula I.

Another aspect of the invention is to use the compounds of the invention to treat or prevent disease states responsive to Vitamin D receptor ligands.

Another aspect of the invention is the prevention and treatment of Acne, Actinic keratosis, Alopecia, Alzheimer's disease, Benign prostatic hyperplasia, Bladder cancer, Bone maintenance in zero gravity, Bone fracture healing, Breast cancer, Chemoprovention of Cancer, Crohn's disease, Colon cancer, Type I diabetes, Host-graft rejection, Hypercalcemia, Type II diabetes, Leukemia, Multiple sclerosis, Myelodysplastic syndrome, Insufficient sebum secretion, Osteomalacia, Osteoporosis, Insufficient dermal firmness, Insufficient dermal hydration, Psoriatic arthritis, Prostate cancer, Psoriasis, Renal osteodystrophy, Rheumatoid arthritis, Scleroderma, Skin cancer, Systemic lupus erythematosus, Skin cell damage from Mustard vesicants, Ulcerative colitis, Vitiligo, or Wrinkles; by administering to a mammal in need thereof a pharmaceutically effective amount of a compound of Formula I.

Another aspect of the invention is the use of the compounds of Formula I for treating or preventing disease states mediated by the Vitamin D receptor.

DETAILED DESCRIPTION OF THE INVENTION

I. Definitions:

The word "adhesion" refers to the abnormal union of surfaces normally separate by the formulation of new fibrous tissue resulting from an inflammatory process.

The word "abscess" is a complication often associated with surgery, trauma, or diseases that predispose the host to abscess formation from encapsulated bacteria lymphocytes, macrophages, and etc.

The term "alkenyl" refers to aliphatic groups wherein the point of attachment is a carbon-carbon double bond, for example vinyl, 1-propenyl, and 1-cyclohexenyl. Alkenyl groups may be straight-chain, branched-chain, cyclic, or combinations thereof, and may be optionally substituted. Suitable alkenyl groups have from 2 to about 20 carbon atoms.

The term "alkoxy" refers to —OR wherein R is an aliphatic or aromatic group which may be optionally substituted. Methoxy, ethoxy, propoxy, butoxy, and phenoxy are examples of alkoxy groups.

The term "alkyl" refers to saturated aliphatic groups including straight-chain, branched-chain, cyclic and any combinations thereof. Alkyl groups may further be divided into "primary", "secondary", and "tertiary" alkyl groups. In primary alkyl groups, the carbon atom of attachment is substituted with zero (methyl) or one organic radical. In secondary alkyl groups, the carbon atom of attachment is substituted with two organic radicals. In tertiary alkyl groups, the carbon atom of attachment is substituted with three organic radicals.

The term "cycloalkyl" includes organic radicals such as cyclopropanyl, cyclobutanyl, and cyclopentyl.

The term, "cycloalkenyl" includes organic radicals such as cyclopropenyl, cyclobutenyl, cyclopentenyl, and cyclohexenyl.

The term, "$C_1$-$C_5$ fluoroalkyl" refers to an alkyl group containing fluorine and includes organic radicals such as —$CF_3$, —$CHF_2$, —$CH_2F$, —$CF_2CF_3$, —$CHFCF_3$, —$CH_2CF_3$, —$CH_2CHF_2$, and —$CH_2CH_2F$, with —$CF_3$ being preferred.

The term, "Active Ingredient" refers to a compound of the invention represented by any of (i) formulae I, II, III, IV, (ii) the product of any example set out herein, or (iii) a compound identified in any row of Tables 1, 2, 3, or 4; or a salt or prodrug derivative of the preceding compound.

The term "carboxamide" refers to a group represented by the formulae:

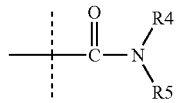

where R4 and R5 are independently hydrogen, $C_1$-$C_4$ alkyl, —O—$C_1$-$C_4$ alkyl, $C_2$-$C_4$ alkenyl, $C_2$-$C_4$ alkynyl, $C_1$-$C_4$ haloalkyl, —NH($C_1$-$C_4$ alkyl), or cyclopropyl, with the proviso that only one of R4 or R5 may be hydrogen.

The abbreviation, "Me" means methyl.
The abbreviation, "Et" means ethyl.
The abbreviation, "iPr" means 1-methylethyl.
The abbreviation, "tbu" means 1,1-dimethylethyl.
The symbol "-(CH2)2- is equivalent to —$CH_2$—$CH_2$—.
The univalent symbol "—O" in any structural formula is a hydroxyl group (—OH).

The term, "$C_{1-3}$ alkyl" refers to an alkyl group selected from methyl, ethyl, n-propyl, and isopropyl.

The term, "branched $C_3$-$C_5$ alkyl" is an alkyl group selected from 1-methylethyl; 1-methylpropyl; 2-methylpropyl; 1,1-dimethylethyl; 1,1-dimethylpropyl; 1,2-dimethylpropyl; or 2,2-dimethylpropyl. Preferred branched $C_3$-$C_5$ alkyl groups are 2-methylpropyl and 1,1-dimethylethyl, with the 1,1-dimethylethyl group being most preferred.

The term "alkenyl" refers to aliphatic groups wherein the point of attachment is a carbon-carbon double bond, for example vinyl, 1-propenyl, and 1-cyclohexenyl. Alkenyl groups may be straight-chain, branched-chain, cyclic, or combinations thereof, and may be optionally substituted. Suitable alkenyl groups have from 2 to about 20 carbon atoms.

The term "$C_1$-$C_5$ alkyl" refers to saturated aliphatic groups including straight-chain, branched-chain, and cyclic groups and any combinations thereof. Alkyl groups may further be divided into "primary", "secondary", and "tertiary" alkyl groups. In primary alkyl groups, the carbon atom of attachment is substituted with zero (methyl) or one organic radical. In secondary alkyl groups, the carbon atom of attachment is substituted with two organic radicals. In tertiary alkyl groups, the carbon atom of attachment is substituted with three organic radicals. Examples of $C_1$-$C_5$ alkyl groups are methyl, ethyl, n-propyl, from 1-methylethyl; n-butyl, 1-nethylpropyl; 2-methylpropyl; 1,1-dimethylethyl; n-amyl, 1,1-dimethylpropyl; 1,2-dimethylpropyl; and 2,2-dimethylpropyl.

The term "cycloalkyl" includes organic radicals such as cyclopropyl, cyclobutyl, cyclopentyl and cyclohexyl.

The term, "cycloalkenyl" includes organic radicals such as cyclopropenyl, cyclobutenyl, cyclopentenyl and cyclohexenyl.

The term, "$C_1$-$C_5$ fluoroalkyl" is an alkyl group containing fluorine and includes organic radicals such as —$CF_3$, —$CHF_2$, —$CH_2F$, —$CF_2CF_3$, —$CHFCF_3$, —$CH_2CF_3$, —$CH_2CHF_2$, and —$CH_2CH_2F$, with —$CF_3$ being preferred.

The abbreviation, "Me" means methyl.
The abbreviation, "Et" means ethyl.
The abbreviation, "iPr" means 1-methylethyl.
The abbreviation, "tBu" means 1,1-dimethylethyl.

The term, "terminal hydroxyalkyl" refers to a group selected from
    3-methyl-3-hydroxypentyl,
    3-methyl-3-hydroxypentenyl, 3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
1-hydroxy-2-methyl-1-(methylethyl)propyl,
1-hydroxy-2,2-dimethylpropyl,
1-hydroxy-1,2,2-trimethylpropyl,
1-hydroxycycloalkenyl; and
1-hydroxycycloalkyl.

The term, "3-methyl-3-hydroxypentyl" refers to the radical having the structural formula:

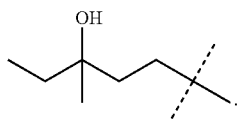

The term, "3-methyl-3-hydroxypentenyl" refers to the radical having the structural formula (both cis and trans isomers):

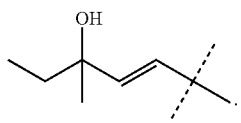

The term, "3-methyl-3-hydroxypentynyl" refers to the radical having the structural formula:

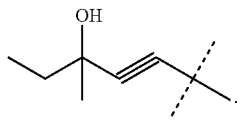

The term, "3-ethyl-3-hydroxypentyl" refers to the radical having the structural formula:

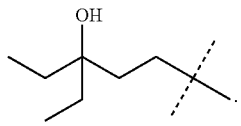

The term, "3-ethyl-3-hydroxypentenyl" refers to the radical having the structural formula (both cis and trans isomers):

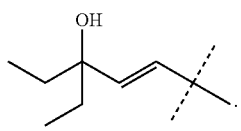

The term, "3-ethyl-3-hydroxypentynyl" refers to the radical having the structural formula:

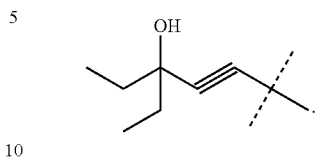

The term, "3-propyl-3-hydroxypentyl" refers to the radical having the structural formula:

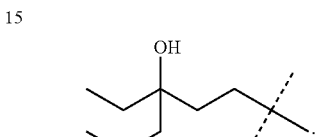

The term, "3-propyl-3-hydroxypentenyl" refers to the radical having the structural formula (both cis and trans isomers):

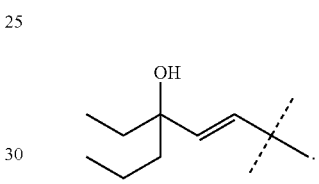

The term, "3-propyl-3-hydroxypentynyl" refers to the radical having the structural formula:

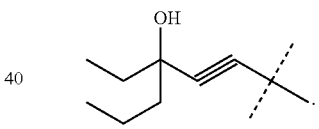

The term, "3-ethyl-3-hydroxy-4-methylpentyl" refers to the radical having the structural formula:

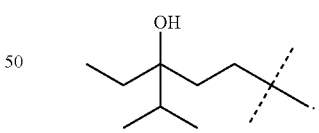

The term, "3-ethyl-3-hydroxy-4-methylpentenyl" refers to the radical having the structural formula (both cis and trans isomers):

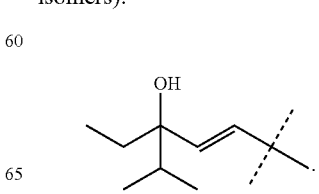

The term, "3-ethyl-3-hydroxy-4-methylpentynyl" refers to the radical having the structural formula:

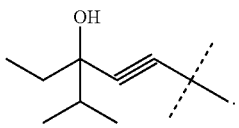

The term, "1-hydroxy-2-methyl-1-(methylethyl)propyl" refers to the radical having the structural formula:

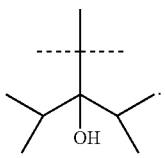

The term, "1-hydroxy-2,2-dimethylpropyl" refers to the radical having the structural formula:

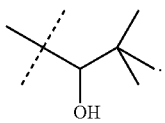

The term, "1-hydroxy-1,2,2-trimethylpropyl" refers to the radical having the structural formula:

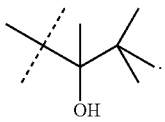

The term, "1-hydroxycycloalkenyl" refers to a radical selected from 1-hydroxycyclopentenyl, 1-hydroxycyclohexenyl, 1-hydroxycycloheptenyl, or 1-hydroxycyclooctenyl.

The term "hydroxycycloalkyl" refers to a radical having the general structural formula:

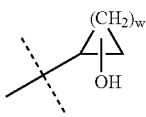

where w is an integer from 1 to 6 and the hydroxyl radical is substituted on any ring carbon atom.

The term "1-hydroxycycloalkyl" refers to a radical having the general structural formula:

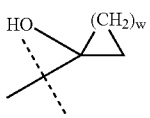

Examples of 1-hydroxycycloalkyl radicals are 1-hydroxycyclopropyl, 1-hydroxycyclobutyl, 1-hydroxycyclopentyl, 1-hydroxycyclohexyl, 1-hydroxycycloheptyl, and 1-hydroxycyclooctyl.

The abbreviation, "Me" means methyl.
The abbreviation, "Et" means ethyl.
The abbreviation, "iPr" means 1-methylethyl.
The abbreviation, "nPr" means n-propyl.
The abbreviation, "3Me3OH-Pentyl" means 3-methyl-3-hydroxypentyl.
The abbreviation, "3Me3OH-Pentenyl" means 3-methyl-3-hydroxypentenyl
The abbreviation, "3Me3OH-Pentynyl" means 3-methyl-3-hydroxypentynyl
The abbreviation, "3Et3OOH-Pentyl" means 3-ethyl-3-hydroxypentyl.
The abbreviation, "3Et3OH-Pentenyl" means 3-ethyl-3-hydroxypentenyl
The abbreviation, "3Et3OH-Pentynyl" means 3-ethyl-3-hydroxypentynyl
The abbreviation, "3Pr3OH-Pentyl" means 3-propyl-3-hydroxypentyl.
The abbreviation, "3Pr3OH-Pentenyl" means 3-propyl-3-hydroxypentenyl.
The abbreviation, "3Pr3OH-Pentynyl" means 3-propyl-3-hydroxypentynyl.
The abbreviation, "3Et3OH4Me-Pentyl" means 3-ethyl-3-hydroxy-4-methylpentyl.
The abbreviation, "3Et3OH4Me-Pentenyl" means 3-ethyl-3-hydroxy-4-methylpentenyl,
The abbreviation, "3Et3OH4Me-Pentynyl" means 3-ethyl-3-hydroxy-4-methylpentynyl.
The abbreviation, "1OH2Me1MeEt-Propyl" means 1-hydroxy-2-methyl-1-(methylethyl)propyl.

The term "$C_1$-$C_5$ alkyl" is an alkyl substituent selected from the group consisting of: methyl; ethyl; propyl; 1-methylethyl; 1-methylpropyl; 2-methylpropyl; 1,1-dimethylethyl; 1,1-dimethylpropyl; 1,2-dimethylpropyl; and 2,2-dimethylpropyl. The preferred groups are 2-methylpropyl and 1,1-dimethylethyl, with the 1,1-dimethylethyl group being most preferred.

The dotted line symbol crossing a solid line representing a bond

means that the bond so marked is point of attachment.
The term, "mammal" includes humans.
The term "halo" refer to fluorine, chlorine, bromine, and iodine.
The term "pharmaceutically acceptable salt" refers to concentional non-toxic anionic or cationic salts conventionally used in therapeutic compounds, for example, sodium and potassium.

Compounds of the Invention:
The compounds of the invention are Vitamin D Receptor Modulators represented by formula I or a pharmaceutically acceptable salt or prodrug derivative thereof:

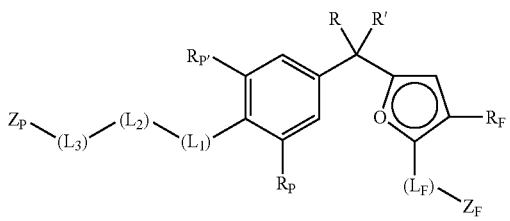

wherein;

R and R' are independently $C_1$-$C_4$ alkyl, $C_1$-$C_4$ fluoroalkyl, or together R and R' form a substituted or unsubstituted, saturated or unsaturated carbocyclic ring having from 3 to 8 carbon atoms;

$R_P$, $R_{P'}$, and $R_F$ are independently selected from the group consisting of hydrogen, halo, $C_1$-$C_4$ alkyl, $C_2$-$C_4$ alkenyl, $C_2$-$C_4$ alkynyl, $C_1$-$C_4$ fluoroalkyl, —O—$C_1$-$C_4$ alkyl, —S—$C_1$-$C_4$ alkyl, —O—$C_1$-$C_4$ fluoroalkyl, —CN, —$NO_2$, acetyl, —S—$C_1$-$C_4$ fluoroalkyl, $C_2$-$C_4$ alkenyl, $C_3$-$C_4$ cycloalkyl, and $C_3$-$C_4$ cycloalkenyl;

($L_1$), ($L_2$), ($L_3$), and ($L_F$) are divalent linking groups independently selected from the group consisting of
a bond,
oxygen

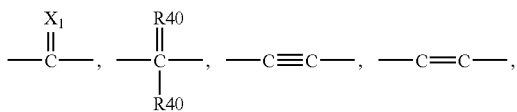

where each R40 is independently hydrogen, $C_1$-$C_5$ alkyl or $C_1$-$C_5$ fluoroalkyl;

where X1 is O, CH2 or [H, OH];

$Z_F$ is

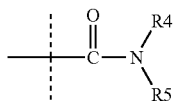

where R4 and R5 are independently hydrogen, $C_1$-$C_4$ alkyl, —O—$C_1$-$C_4$ alkyl, $C_2$-$C_4$ alkenyl, $C_2$-$C_4$ alkynyl, $C_1$-$C_4$ haloalkyl, —NH($C_1$-$C_4$ alkyl), or cyclopropyl, with the proviso that only one of R4 or R5 may be hydrogen.

$Z_P$ is
methyl,
ethyl,
n-propyl,
1-methylethyl,
1-methylpropyl,
2-methylpropyl,
1,1-dimethylethyl,
1,1-dimethylpropyl,
1,2-dimethylpropyl,
2,2-dimethylpropyl,
1-hydroxy-2,2-dimethylpropyl,
1-hydroxy-1,2,2-trimethylpropyl,
2-hydroxy-2-methylbutoxy
2-hydroxy-2-ethylbutoxy
2-hydroxy-2-ethyl-3-methylbutoxy
2-hydroxy-2-methyl-3-methylbutoxy
2-hydroxy-1,3,3-trimethylbutoxy
2-hydroxy-1-ethyl-3,3-dimethylbutoxy
2-hydroxy-1,2-diethylbutoxy
2-hydroxy-2-ethyl-1-methylbutoxy
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
1-hydroxy-2-methyl-1-(methylethyl)propyl
1-hydroxycycyclopentenyl,
1-hydroxycyclohexenyl,
1-hydroxycycloheptenyl,
1-hydroxycyclooctenyl,
1-hydroxycyclopropyl,
1-hydroxycyclobutyl,
1-hydroxycyclopentyl,
1-hydroxycyclohexyl,
1-hydroxycycloheptyl, or
151-hydroxycyclooctyl.

Preferred compounds of the invention are when $Z_P$ is 1,1-dimethylethyl, 1,2-dimethylpropyl, 2,2-dimethylpropyl, 1-hydroxy-2,2-dimethylpropyl, and 1-hydroxy-1,2,2-trimethylpropyl; provided that ($L_1$), ($L_2$), ($L_3$) are all bonds (viz., $Z_P$ is attached directly to the phenyl ring of the nucleus).

Preferred compound have $Z_F$ selected from:
—C(O)NHMe,
—C(O)NHEt,
—C(O)NH(iPr),
—C(O)NH(tBu),
—C(O)NH($CF_3$),
—C(O)N(Me)$_2$,
—C(O)NMeEt,
—C(O)NMe(iPr),
—C(O)NMe(tBu),
—C(O)NMe($CF_3$),
—C(O)N(Me)F,
—C(O)N(Et)F
—C(O)N(iPr)F,
—C(O)N(tBu)F,
—C(O)N(Et)$_2$,
—C(O)NEt(iPr), or
—C(O)NEt(tBu).

Other preferred compounds have $Z_F$ selected from:
—C(O)NHMe,
—C(O)NHEt,
—C(O)NH(iPr),
—C(O)NH(tBu),
—C(O)N(Me)$_2$,
—C(O)NMeEt,
—C(O)NMe(iPr),
—C(O)NMe(tBu),
—C(O)N(Et)$_2$,
—C(O)NEt(iPr), or
—C(O)NEt(tBu).

A preferred carboxamide group $Z_F$ is

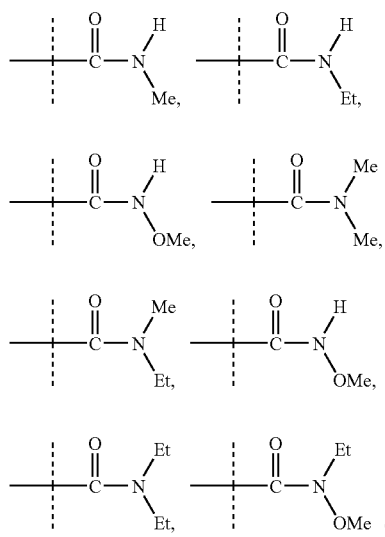
Preferred Compounds of the Invention are represented by formulae A to K as follows:
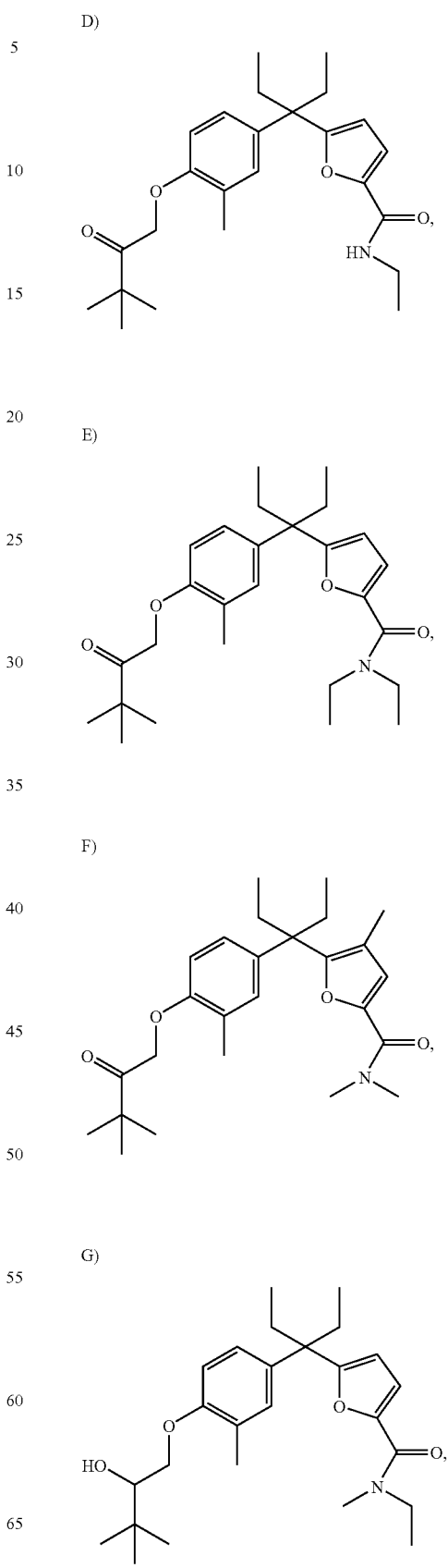

H)

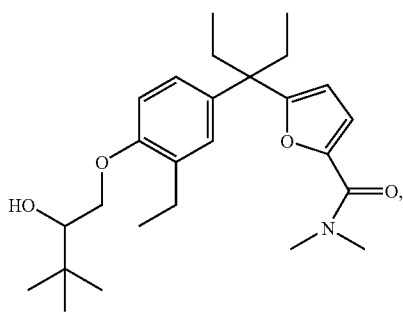

I)

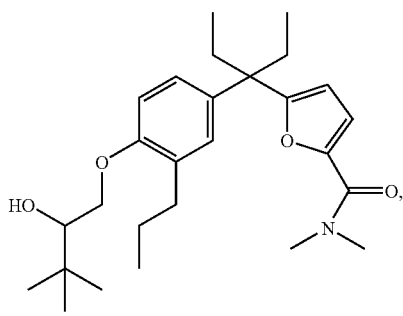

J)

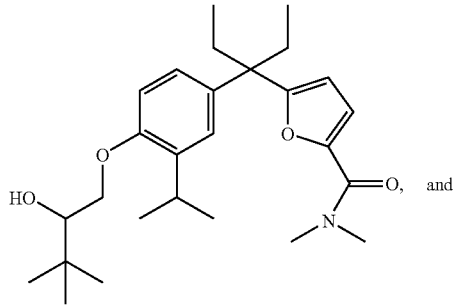

and

K)

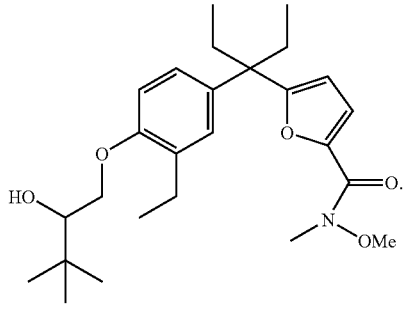

EXAMPLES

General Experimental Conditions:

The starting material/intermediate is the compound from the immediate preceding experimental unless otherwise indicated.

All reactions are performed under nitrogen/argon atmosphere, in a stirred reaction vessel, and at room temperature unless indicated otherwise.

Concentration is performed from RT to about 70° C. under vacuum (0.05 to 1 mm Hg).

Unless otherwise indicated, the organic layer is MgSO4/Na2SO4 dried is defined as stirring the solution with a dessicant for 5-15 m and filtering off the dessicant to give an anhydrous filtrate.

For analogous multi-step reaction procedures, the yield is given either for the ultimate step or overall multi-steps as indicated.

Solutions are "concentrated" at a range of 25-75° C. with reduced pressure. in-vacuo −25-75° C.; 0.05 to 1 mm Unless otherwise indicated, "the residue is chromatographed" is defined as silica gel chromatography of residue with moderate nitrogen pressure (flash chromatography) or a medium pressure chromatography systems using a silica gel to crude product ratio of ~10-100.

Thin layer chromatography is performed with silica gel plates with UV and/or appropriate staining solution.

NMR spectra are obtained with either 300 or 400 mHz spectrometer.

NMR—denotes NMR spectrum is consistent with assigned structure.

HRMS—high resolution mass spectrum

ES-MS—electrospray mass spectrum

Abbreviations:
Aq—aqueous
d—day
eq—equivalent
h—hour
m—minute
satd—saturated
disp—dispersion
quant—quantitative
rt for retention time (both small caps to minimize confusion with RT)
RT—room temperature
Chemical Definitions:
BnBr—benzyl bromide
$CH_2Cl_2$—dichloromethane
CH3CN—acetonitrile
DIBA1H—Diisobutyl Aluminum Hydride
DMAP—4-(dimethylamino)pyridine
DMF—N,N-dimethylformamide
DMSO—dimethylsulfoxide
DPPB—1,4-bis(diphenylphosphino)butane
DPPF—dichloro[1,1'-bis(diphenylphosphino)ferrocene
EDCI—3-Ethyl-1-[3-(dimethylamino)propyl]carbodiimide hydrochloride
Et3N—triethylamine
EtMgBr—ethyl magnesium bromide
EtOAc—ethyl acetate
EtOH—ethanol
H2NCH2CO2Me—methyl glycinate
Hept—heptane
Hex—hexanes
HN(OMe)Me—N-methyl-O-methyl hydroxylamine
HNMe2—dimethyl amine
HATU—O-(7-azabenzotriazol-1-yl)-N,N,N',N'-tetramethyluronium hexafluorophosphate
HOAT—7-aza-1-hydroxybenzotriazole
HOBT—1-hydroxybenzotriazole
K2CO3—potassium carbonate
KOH—potassium hydroxide
LAH—lithium aluminum hydride
LiHMDS—lithium hexamethyldisilazide
mCPBA—meta-chloroperbenzoic acid MeI—methyl iodide
MeOH—methanol
NaBH4—sodium borohydride
MgSO4—magnesium sulfate
NaH—sodium hydride
NaHCO3—sodium bicarbonate
NaI—sodium iodide
Na2SO4—sodium sulfate
NH4Cl—ammonium chloride
NMO—4-methylmorpholine N-oxide
NMP—N-methylpyrrolidin-2-one
Na—S—R3—sodium alkylmercaptide
PBr3—phosphorus tribromide
Pd(DPPF)—palladium dichloro[1,1'-bis(diphenylphosphino)ferrocene
Pd(OAc)2—palladium (II) acetate
Pd(TPP)4—palladium tetrakistriphenylphosphine
Pd—C—palladium on carbon
(PhO)2P(O)N3—diphenyl phosphorus azide
pTSA—para-toluenesulfonic acid
Pyr—pyridine
Red-Al—sodium bis(2-methoxyethoxy)aluminum hydride
R2MgBr—alkyl magnesium bromide
R3MgBr—alkyl magnesium bromide
R5MgBr—alkyl magnesium bromide
R2S(O)2NH2—alkylsulfonamide
TBAF—tetrabutylammonium fluoride
TBSCl—tert-butyldimethylsilyl chloride
tBuC(O)CH2Br—1-bromopinacolone
Tf2O—triflic anhydride
TFA—trifluoroacetic acid
THF—tetrahydrofuran
TPAP—tetrapropylammonium perruthenate
Zn(OTf)2—zinc trifluoromethane sulfonate.

Compounds of the Invention—Salts, Stereoisomers, & Prodrugs:

Salts of the compounds represented by formulae I are an additional aspect of the invention. The skilled artisan will also appreciate that the family of compounds of formulae I include acidic and basic members and that the present invention includes pharmaceutically acceptable salts thereof.

In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, ammonium, calcium, magnesium, aluminum, zinc, and the like. Sodium and potassium saltgs are particularly preferred. Salts are conveniently prepared from the free acid by treating the acid in solution with a base or by exposing the acid to an ion exchange resin. For example, a carboxylic acid substituent on the compound of Formula I may be selected as —CO₂H and salts may be formed by reaction with appropriate bases (e.g., NaOH, KOH) to yield the corresponding sodium and potassium salt.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, choline, clavulanate, citrate, chloride, chloroprocaine, choline, diethanolamine, dihydrochloride, diphosphate, edetate, edisylate, estolate, esylate, ethylenediamine, fluoride, fumarate, gluceptate, gluconate, glutamate, glycolylarsanilate, hexylresorcinate, hydrabamine, bromide, chloride, hydrobromide, hydrochloride, hydroxynaphthoate, iodide, isothionate, lactate, lactobionate, laurate, malate, maleate, malseate, mandelate, meglumine, mesylate, mesviate, methylbromide, methylnitrate, methylsulfate, mucate, napsylate, nitrate, oleate, oxalate, palmitate, pamoate, pantothenate, phosphate, polygalacturonate, procane, salicylate, stearate, subacetate, succinate, sulfate, tannate, tartrate, teoclate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a chiral column may be used such as those sold by Daicel Chemical Industries identified by the trademarks:
CHIRAL AK AD, CHIRALPAK AS, CHIRALPAK OD, CHIRALPAK OJ, CHIRALPAK OA, CHIRALPAK OB, CHIRALPAK OC, CHIRAIPAK OF, CHIRALPAK OG, C ALPAK OK, and CHIRALPAK CA-1.

By another conventional method, a racemic mixture may be reacted with a single enantiomer of some other compound. This changes the racemic form into a mixture of diastereomers. These diastereomers, because they have different melting points, different boiling points, and different solubilities can be separated by conventional means, such as crystallization.

The present invention is also embodied in mixtures of compounds of formulae I.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine.

Pharmaceutical Formulations Containing the Novel Compounds of the Invention:

Pharmaceutical formulations of the invention are prepared by combining (e.g., mixing) a therapeutically effective amount of the compound of the invention (compounds of Formula I) together with a pharmaceutically acceptable carrier or diluent. The present pharmaceutical formulations are prepared by known procedures using well-known and readily available ingredients.

In making the compositions of the present invention, the compounds of Formula I will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the compound. The compounds of the present invention are preferably formulated prior to administration.

The compounds of the invention may also be delivered by suitable formulations contained in a transderm patch. Alternatively, the compounds of the invention may be delivered to a patient by sublingual administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided Active ingredient. In tablets the compound of Formula I is mixed with a carrier having the necessary binding properties in suitable proportions and compacted in the shape and size desired. The powders and tablets preferably contain from about 1 to about 99 weight percent of the compound which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active Ingredient may be dissolved or suspended in a pharmaceutically acceptable carrier, such as sterile water, sterile organic solvent or a mixture of both. The compounds can often be dissolved in a suitable organic solvent, for instance aqueous propylene glycol. Other compositions can be made by dispersing the finely divided compounds of the invention in aqueous starch or sodium carboxymethyl cellulose solution or in a suitable oil.

Methods of Using the Compounds of the Invention:

Many disease states are benefited by treatment with the compounds of Formula I include, but are not limited to:

disease states characterized by abnormal calcium regulation disease states characterized by abnormal cell proliferation disease states characterized by abnormal cell differentiation disease states characterized by abnormal immune response disease states characterized by abnormal dermatological conditions disease states characterized by neurodegenerative condition disease states characterized by inflammation disease states characterized by vitamin D sensitivity disease states characterized by hyperproliferative disorders.

Specific disease states benefited by treatment of the compounds of Formula I and II include, but are not limited to:

Acne
Actinic keratosis
Alopecia
Alzheimer's disease
Benign prostatic hyperplasia
Bladder cancer
Bone maintenance in zero gravity
Bone fracture healing
Breast cancer
Chemoprovention of Cancer
Crohn's disease
Colon cancer
Type I diabetes
Host-graft rejection
Hypercalcemia
Type II diabetes
Leukemia
Multiple sclerosis
Myelodysplastic syndrome
Insufficient sebum secretion
Osteomalacia
Osteoporosis
Insufficient dermal firmness
Insufficient dermal hydration
Psoriatic arthritis
Prostate cancer
Psoriasis
Renal osteodystrophy
Rheumatoid arthritis
Scleroderma
Skin cancer
Systemic lupus erythematosus
Skin cell damage from Mustard vesicants
Ulcerative colitis
Vitiligo
Wrinkles Particularly preferred is the treatment of psoriasis and osteoporosis by administration to a mammal (including a human) of a therapeutically effective amount of compounds of Formulae I. By "pharmaceutically effective amount" it is meant that quantity of pharmaceutical agent corresponding to formulae I which prevents, removes or reduces the deleterious effects of a disease state in mammals, including humans.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a pharmaceutically effective amount typically in the range of from about 0.0001 mg/kg/day to about 50 mg/kg/day of body weight of an active compound of this invention. Preferably the dose of compounds of the invention will be from 0.0001 to 5 mg/kg/day of body weight.

Preferably compounds of the invention (e.g., per Formula I) or pharmaceutical formulations containing these compounds are in unit dosage form for administration to a mammal. The unit dosage form can be a capsule or tablet itself, or the appropriate number of any of these. The quantity of Active ingredient in a unit dose of composition may be varied or adjusted from about 0.0001 to about 1000 milligrams or more according to the particular treatment involved. It may be appreciated that it is necessary to make routine variations to the dosage depending on the age and condition of the patient. Dosage will also depend on the route of administration. The compounds of the invention may be administered by a variety of routes including oral, aerosol, rectal, transdermal, sublingual, subcutaneous, intravenous, intramuscular, and intranasalt Particularly preferred is the treatment of psoriasis with an ointment type formulation containing the compounds of the invention. The ointment formulation may be applied as needed, typically from one to 6 times daily.

Treatment of psoriasis is preferably done with topical application by a formulation in the form of a cream, oil, emulsion, paste or ointment containing a therapeutically effective amount of a compound of the invention. The formulation for topical treatment contains from 0.5 to 0.00005 weight percent, preferably from 0.05 to 0.0005 weight percent, and most preferably from 0.025 to 0.001 of a Active Ingredient.

For example, two semisolid topical preparations useful as vehicles for VDR modulators in treatment and prevention of psoriasis are as follows:

Polyethylene Glycol Ointment USP (p. 2495)
Prepare Polyethylene Glycol Ointment as follows:

| Polyethylene Glycol 3350 | 400 g. |
| Polyethylene Glycol 400 | 600 g. |
| To make | 1000 g. |

Heat the two ingredients on a water bath to 65 C. Allow to cool, and stir until congealed. If a firmer preparation is desired, replace up to 100 g of the polyethylene glycol 400 with an equal amount of polyethylene glycol 3350.

Hydrophilic Ointment USP (p. 1216)
Prepare Hydrophilic Ointment as follows:

| Methylparaben | 0.25 g. |
| Propylparaben | 0.15 g. |
| Sodium Lauryl Sulfate | 10 g. |
| Propylene Glycol | 120 g. |
| Stearyl Alcohol | 250 g. |
| White Petrolatum | 250 g. |
| Purified Water | 370 g. |
| To make about | 1000 g. |

The Stearyl Alcohol and White Petrolatum are melted on a steam bath, and warmed to about 75 C. The other ingredients, previously dissolved in the water are added, warmed to 75 C, and the mixture stirred until it congeals.

For each of the above formulations the Active Ingredient is added during the heating step in an amount that is from 0.5 to 0.00005 weight percent, preferably from 0.05 to 0.0005 weight percent, and most preferably from 0.025 to 0.001 weight percent of the total ointment weight. (Source:— United States Pharmacopoeia 24, United States Pharmacopeial Convention, 1999)

Conventional therapy for osteoporosis includes; (i) estrogens, (ii) androgens, (iii) calcium supplements, (iv) vitamin D metabolites, (v) thiazide diuretics, (vi) calcitonin, (vii) bisphosphonates, (viii) SERMS, and (ix) fluorides (see, Harrison's Principles of Internal Medicine, $13^{th}$ edition, 1994, published by McGraw Hill Publ., ISBN 0-07-032370-4, pgs. 2172-77; the disclosure of which is incorporated herein by reference.). Any one or combination of these conventional therapies may be used in combination with the method of treatment using compounds of Formulae I as taught herein. For example, in a method of treating osteoporosis, the vitamin D receptor modulator compounds of the invention (e.g., as defined by formula I) may be administered separately or simultaneously with a conventional therapy. Alternatively, the vitamin D receptor modulator compounds of the invention may be combined with conventional therapeutic agents in a formulation for treatment of osteoporosis such as set out below:

A formulation for treating osteoporosis comprising:
Ingredient (A1): a vitamin D receptor modulator represented by formula (I), or a pharmaceutically acceptable salt or prodrug derivative thereof;
Ingredient (B 1): one or more co-agents that are conventional for treatment osteoporosis selected from the group consisting of:
a. estrogens,
b. androgens,
c. calcium supplements,
d. vitamin D metabolites,
e. thiazide diuretics,
f. calcitonin,
g. bisphosphonates,
h. SERMS, and
i. fluorides; and
Ingredient (C1): optionally, a carrier or diluent.

Typically useful formulations are those wherein the weight ratio of (A1) to (B1) is from 10:1 to 1:1000 and preferably from 1:1 to 1:100.

Combination Therapy for Psoriasis:

Conventional therapy for psoriasis includes topical glucocorticoids, salicylic acid, crude coal tar, ultraviolet light, and methotrexate (see, Harrison's Principles of Internal Medicine, $13^{th}$ edition, 1994, published by McGraw Hill Publ., ISBN 0-07-032370-4, pgs. 2172-77). Any one or combination of these conventional therapies may be used in combination with the method of treatment using compounds of Formulae I as taught herein. For example, in a method of treating osteoporosis, the vitamin D receptor modulator compounds of the invention (e.g., as defined by formula I) may be topically administered separately or simultaneously with a conventional therapy. Alternatively, the vitamin D receptor modulator compounds of the invention may be combined with conventional therapeutic agents in a topically applied formulation for treatment of osteoporosis such as set out below:

A formulation for treating psoriasis comprising:
Ingredient (A2): a vitamin D receptor modulator represented by formula (I), or a pharmaceutically acceptable salt or prodrug derivative thereof;
Ingredient (B2): one or more co-agents that are conventional for treatment psoriasis selected from the group consisting of:
a. topical glucocorticoids,
b. salicylic acid, or
c. crude coal tar.
Ingredient (C2): optionally, a carrier or diluent.

Typically useful formulations are those wherein the weight ratio of (A2) to (B2) is from 1:10 to 1:100000 and preferably from 1:100 to 1:10000.

General Procedures
Scheme I
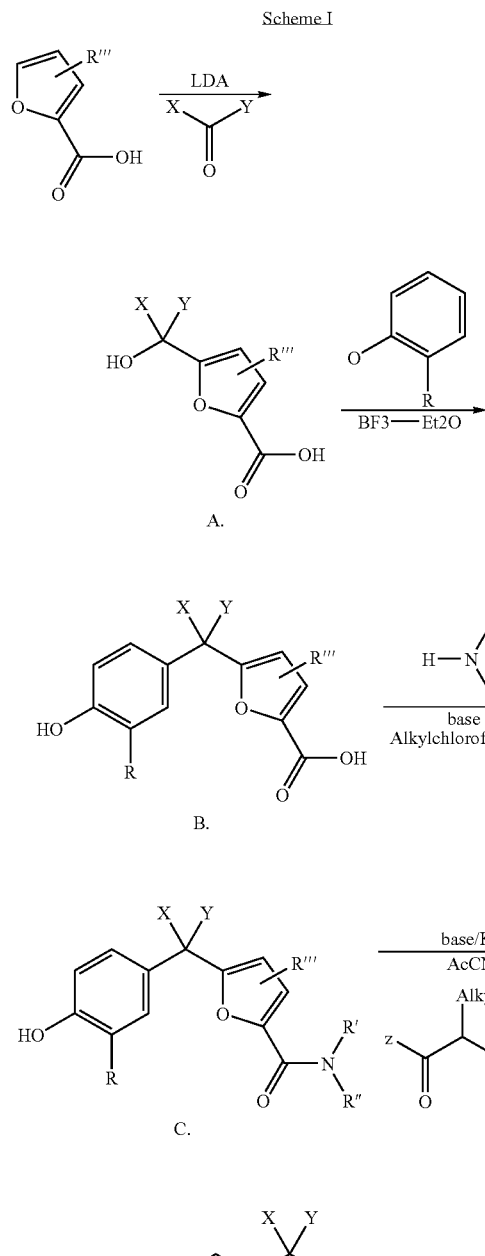
Scheme II
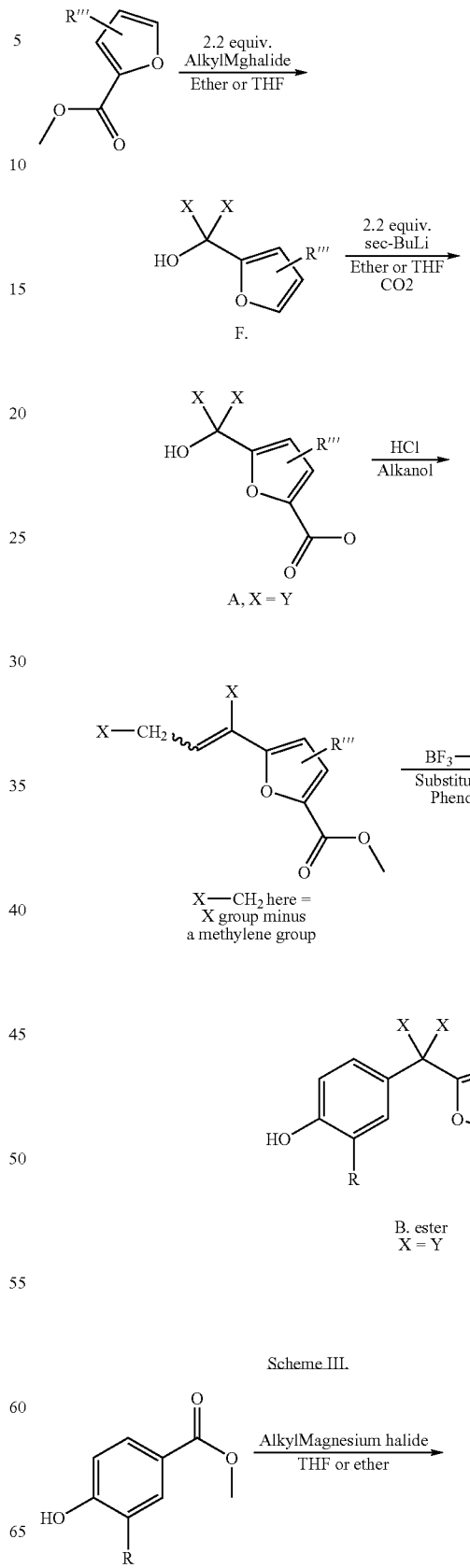

-continued
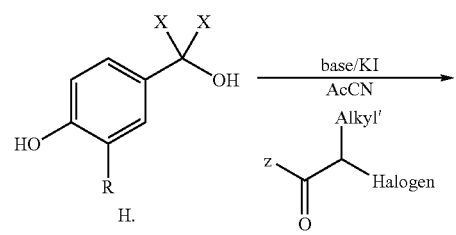
H.
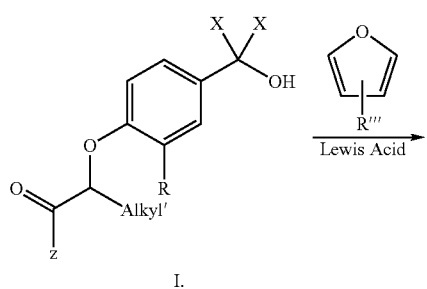
I.
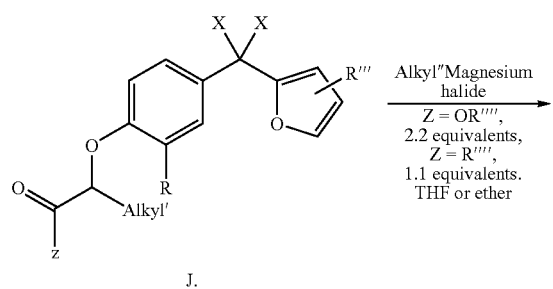
J.
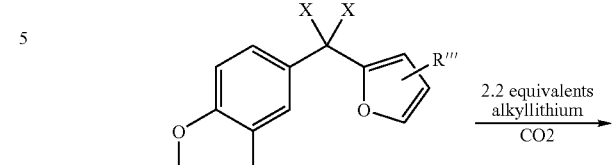
K.
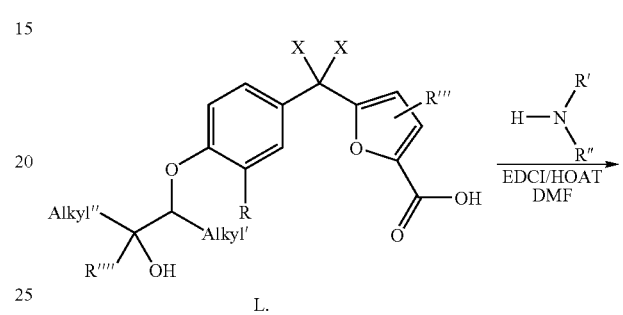
L.
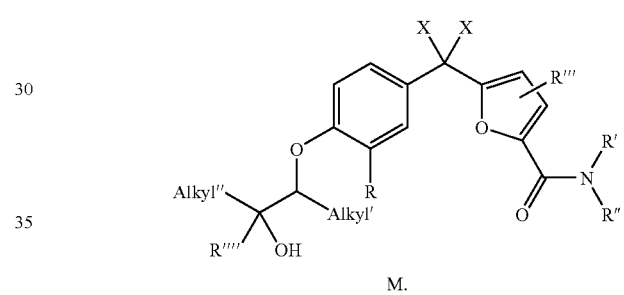
M.
Scheme IV
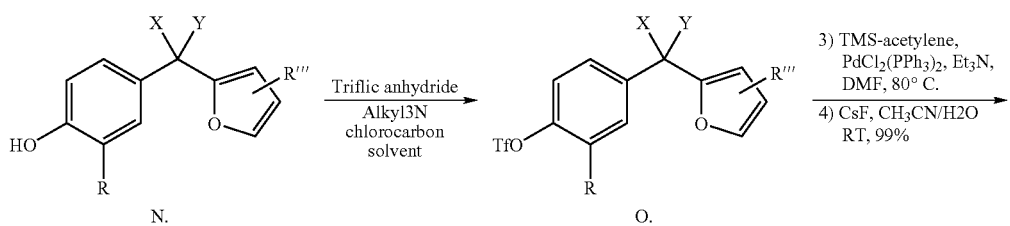
N.                                O.
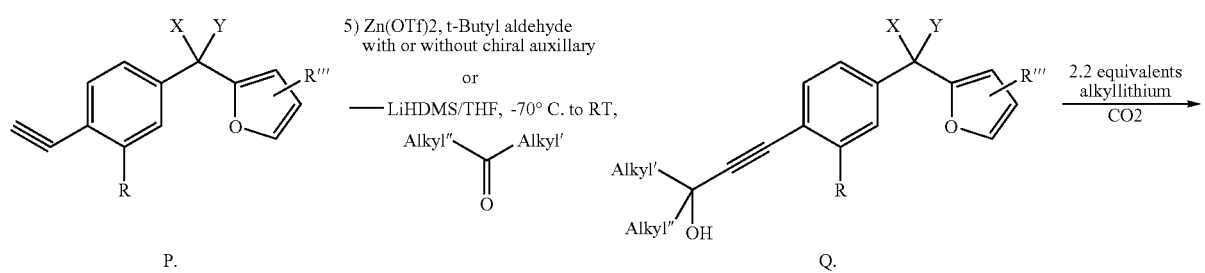
P.                                Q.

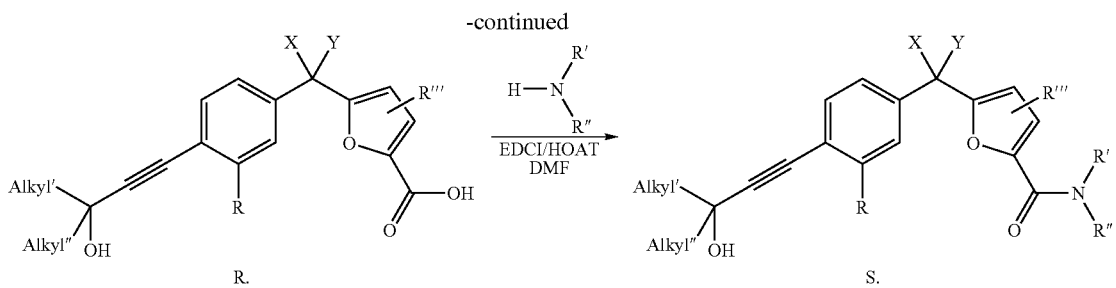

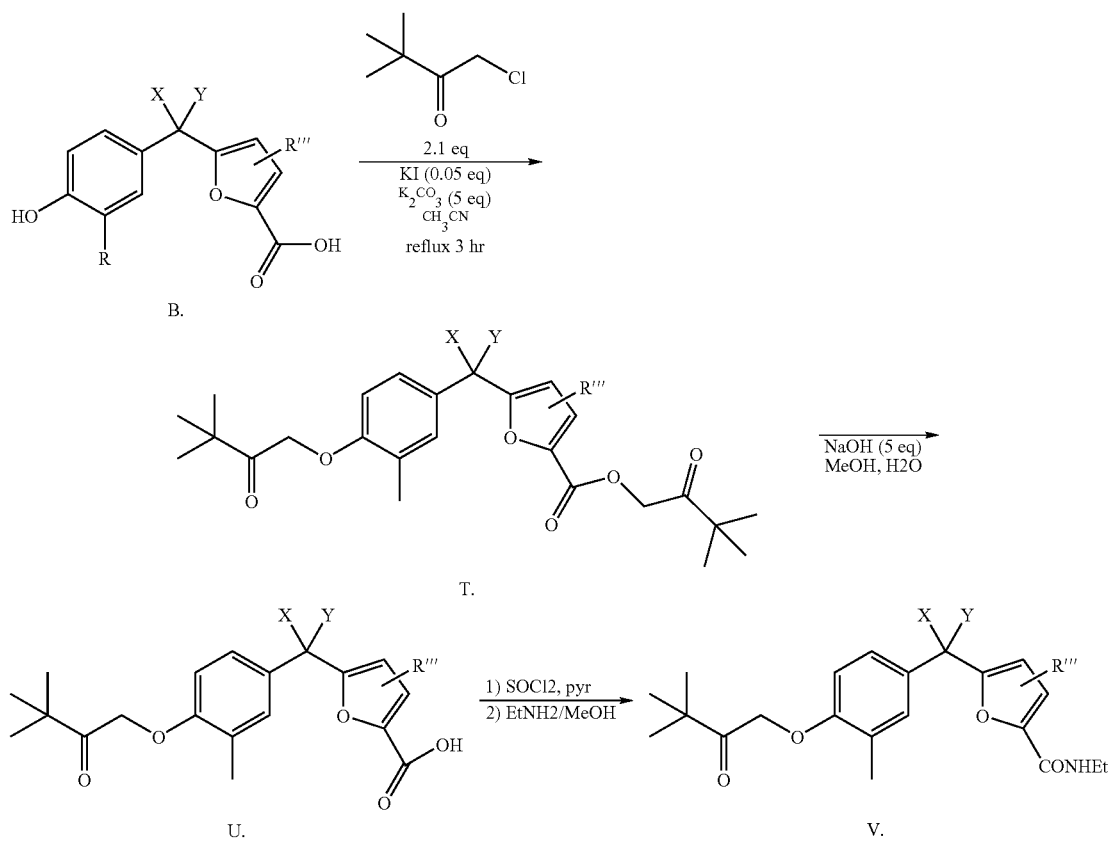

General Procedures

Scheme I. To a furan-2-carboxylic acid is added lithium diisopropylamine (2-2.5 equivalents) from −80 to 0° C. in diethylether or THF solvent under nitrogen. A substituted ketone is added and the mixture is brought to room temperature from 1 to 48 h. The mixture is worked up from ether and water to give the carbinol A. The carbinol A. is reacted with an o-substituted phenol (0.9 to 5 equivalents) with a Lewis acid, e.g., boron trifluoride etherate (0.01 to 10 equivalents) at from 0° C. to room temperature for 30 min to 48 h. The reaction is worked up from ether and water, removing excess phenol under vacuum to give diarylmethane B. Diarylmethane B. can be activated with an alkylchloroformate and base such as trialkylamines followed by treatment with a substituted primary or secondary amine to give the amide C. Amide C. is alkylated with an α-haloketone in the presence of a base such as sodium hydroxide or potassium carbonate in a polar aprotic solvent to give the amide D. Reduction of amide D. with sodium or lithium borohydride or cyanoborohydride in lower molecular weight alkanols gives the secondary carbinol E. as a racemate. The Racemates, of course, can be separated into enantiomers by chiral chromatography on, e.g., a ChiralPak AD column.

Scheme II. Alternately, the ester of diarylmethane B. can be generally prepared as follows: A furanyl carboxylate is reacted with an alkyl magnesium bromide or alkyl lithium (2.0 to 2.5 equivalents) at from 0° C. to room temperature in ether or THF solvent over 30 min to 48 h to give the tert-carbinol F. The tert-carbinol F. is deprotonated with of an alkyl lithium reagent (1.9 to 2.5 equivalents) at from −80° C. to 0° C. over a period of 10 min to 2 h, then excess carbon dioxide gas is bubbled into the mixture, and the mixture is allowed to come to room temperature from 30 min to 48 h. The mixture is worked up from water and ether to give the carboxylic acid A. The carboxylic acid A. may be simultaneously dehydrated and esterified by heating with an alkanol saturated with hydrogen halides such as hydrogen chloride or hydrogen bromide to give the Z/E-olefin G. The olefin G. like carbinol A. may alkylate a substituted o-phenol in the presence of a Lewis acid, e.g., boron trifluoride etherate (0.01 to 5 equivalents) to give the ester of B, which can be saponified from room temperature to reflux in an alkanol with sodium, potassium, or lithium hydroxide to B.

Scheme III. To a 4-hydroxy-3-alkyl benzoate ester is added alkylmagnesium halide in a reaction analogous to Scheme II, product F. to give the tert-carbinol H. The phenolic H intermediate is alkylated with an alpha-halo ketone or alpha-halo ester in a reaction analogous to Scheme I, product D. to give the intermediate I. Reacting I. with a substituted or unsubstituted furan in the presence of a Lewis acid, such as, boron trifluoride etherate at room temperature for 30 min to 60 h gives the diarylmethane J. The diarylmethane J. is reacted with an excess of Grignard reagent, analogous to the reaction in Scheme II, product F. to produce the intermediate tert-carbinol K. Treatment of carbinol K. with an alkyllithium in a reaction analogous to Scheme II, product A. gives the acid L. The acid L. is coupled with a primary or secondary amine in the presence of a coupling reagent, such as, EDCI/HOAT in a polar aprotic solvent, such as, DMF to give the amide M.

Scheme IV: The synthesis of carbon linked actylenic carbinols S is also described in Scheme IV. The starting material N. is produced from Scheme III intermediate H. and a substituted or unsubstituted furan in the presence of Lewis acid, analogous to the synthesis of Scheme III, product J. Furan N. is reacted with triflic anhydride in a chlorocarbon solvent and trialkylamine base over 30 min to 48 h to give the triflate O. The triflate O. is coupled to TMS-acetylene with palladium in the present of a base, such as CsF or trialkylamine in DMF or acetonitrile/water solvent over 30 min to 48 h from room temperature to 110° C. to produce the acetylene P. Acetylene P. is de-protonated and reacted with a dialkyl ketone or aldehyde to produce the secondary or tert-carbinol Q. The carbinol Q. in reactions analogous to Scheme III, acid L. and amide M. is used to produce the intermediate acid R. and amide S.

Scheme V. The bis-pinacolone T. can be formed by reacting a diaryl B. with t-butyl carbonyl chloride (2.0 to 2.5 equivalents) in the presence of potassium iodide (0.01 to 0.10 equivalents), $K_2CO_3$ (4 to 5 equivalents) and cyanomethane at reflux from about 2 to about 6 hours. The bis-pinacolone T. is dealkylated with a suitable base such as sodium hydroxide (4 to 6 equivalents) in the presence of a suitable solvent such as a methanol/$H_2O$ mixture to provide the pinacolone-acid U. The N-alkyl amide V. can be prepared by activating the pinacolone-acid U. with thionyl chloride in the presence of a suitable amine, such as pyridine and subsequently reacted with a suitable alkyl amine in a suitable organic solvent.

Example 1

Preparation of 3'-[4-(2-oxo-3,3-dimethylbutoxy)-3-methylphenyl]-3'-[5-dimethylaminocarbonyl-2-furanyl]pentane

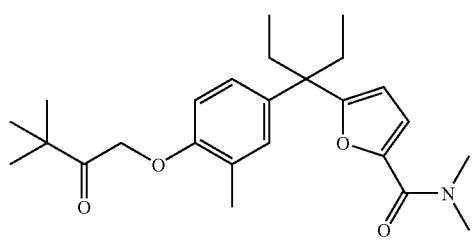

A. 3'-[5-Carboxy-2-furanyl]-3'-hydroxypentane

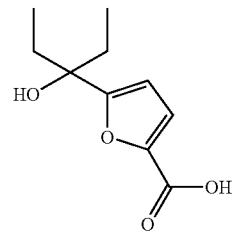

To a solution of i-propylamine (44.8 mL, 0.32 mole) in THF (980 mL) is added 1.6 M n-butyllithium (200 mL, 0.32 mole) in hexanes at −15 to −8° C. with stirring. The mixture is diluted with THF (640 mL) and cooled to −74° C. The 2-furoic acid (17.92 g, 0.16 mole) in THF (320 mL) is added so as to keep the temperature at −70 to −77° C. After 30 min in the cold, 3-pentanone (15.15 g, 0.176 mole) in THF (20 mL) is added dropwise while keeping the temperature below −70° C., and then the reaction mixture is allowed to come to room temperature. The mixture is quenched with water, and most of the THF is removed by evaporation under vacuum. The aqueous residue is extracted with diethylether (2×200 mL) and acidified with 5N HCl. The product is extracted with diethylether (3×600 mL), $MgSO_4$ dried, concentrated, to give the title compound as an oil (31.3 g, 99% crude) which is used as is.

B. 3'-[4-Hydroxy-3-methylphenyl]-3'-[5-carboxy-2-furanyl]pentane

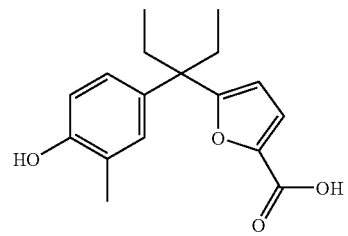

To 3'-[5-carboxy-2-furanyl]-3'-hydroxypentane (5.94 g, 30 mmol) and o-cresol (19.44 g, 180 mmol) in methylene chloride (30 mL) is added borontrifluoride etherate (1.5 ml., 12 mmol) at room temperature under nitrogen. The mixture is stirred for 5 h, and the mixture is partitioned between diethylether (100 mL) and satd sodium carbonate (100 mL). The aqueous phase is washed one more time with diethylether (100 mL). The combined ether layers are extracted twice with satd sodium carbonate (2×30 mL), and the combined aqueous phases are washed with diethylether (2×50 mL) prior to acidification with 5N HCl to pH ~2. The product is extracted into diethylether (2×100 mL), dried over $MgSO_4$, and evaporated under vacuum to give an oil. The residue is crystallized from ethylacetate and isooctane to give the title product as white crystals (5.33 g, 62%).

$^1$H NMR (CDCl$_3$) δ 9.12 (s, 1H), 7.13 (d, 1H, J=3.6 Hz), 6.80 (s, 1H), 6.75 (d, 1H, J=8.2 Hz), 6.68 (d, 1H, J=8.2 Hz), 6.36 (d, 1H, J=3.6 Hz), 2.06 (s, 3H), 1.97 (q, 4H, J=7.0), 0.60 (t, 6H, J=7.0 Hz).

ES/MS: 289.0 (M+1).

C. 3'-[4-Hydroxy-3-methylphenyl]-3'-[5-dimethylaminecarbonyl-2-furanyl]pentane

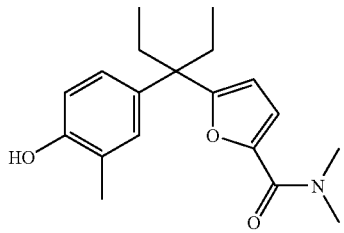

To 3'-[4-hydroxy-3-methylphenyl]-3'-[5-carboxy-2-furanyl]pentane (0.75 g, 2.6 mmol) in THF (50 mL) is added tri-n-butylamine (0.67 mL, 2.86 mmol), and the mixture is cooled in an ice bath. To the cooled solution is added isobutylchloroformate (0.372 mL, 2.86 mmol) dropwise, and it is allowed to stir 5 min. To the mixture is added 2.0 M dimethylamine in methanol (7.8 mL, 15.6 mmol) and the reaction is allowed to come to room temperature and stirred 30 min. The mixture is evaporated under vacuum, and the residue is partitioned between water (100 mL0 and diethylether (100 mL). The organic phase is washed with satd sodium bicarbonate (2×30 mL); with satd brine (30 mL); with 0.3 N HCl (3×30 mL); and with satd brine (10 mL). The organic phase is dried over MgSO$_4$, and evaporated under vacuum to give the title product as an oil (538 mg, 66%)

ES/MS: 316.3 (M+1), 314.2 (M−1).

D. 3'-[4-(2-Oxo-3,3-dimethylbutoxy)-3-methylphenyl]-3'-[5-dimethylaminocarbonyl-2-furanyl]pentane To 3'-[4-hydroxy-3-methylphenyl]-3'-[5-dimethylaminecarbonyl-2-furanyl]pentane (0.53 g, 1.7 mmol) in acetonitrile (15 mL) is added 1-chloropinacolone (0.23 mL, 1.76 mmol), potassium carbonate (1.16 g, 8.4 mmol), and catalytic potassium iodide (14 mg, 0.08 mmol). The mixture is heated at reflux for 45 min; cooled to room temperature; and evaporated under vacuum. The residue is partitioned between methylene chloride and water, and the water layer is extracted one time more with methylene chloride. The combined organic layers are dried over anhydrous magnesium sulfate, filtered, and evaporated under vacuum to give an oil. The residue is crystallized from hexane to give the title compound (0.41 g, 59%)

$^1$H NMR (CDCl$_3$) δ6.92 (m 2H), 6.84 (d, 1H, J=8.0 Hz), 6.62 (d, 1H, J=8.0 Hz), 6.41 (d, 1H, J=3.0 Hz), 5.07 (s, 2H), 2.92 (s, 6H), 2.15 (s, 3H), 2.00 (q, 4H, J=7.6 Hz), 1.16 (s, 9H), 0.61 (t, 6H, J=7.6 Hz).

ES/MS: 414.2 (M+1).

Example 2

Preparation of 3'-[4-(2-hydroxy-3,3-dimethylbutoxy)-3-methylphenyl]-3'-[5-dimethylaminocarbonyl-2-furanyl]pentane

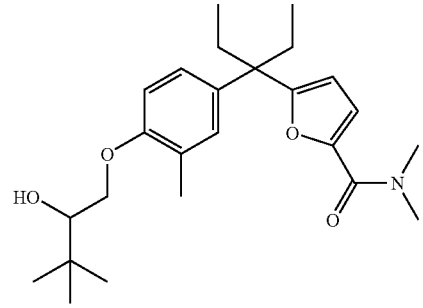

3'-[4-(2-Oxo-3,3-dimethylbutoxy)-3-methylphenyl]-3'-[5-dimethylaminocarbonyl-2-furanyl]pentane (0.32 g, 0.79 mmol) and sodium borohydride (30 mg, 0.79 mmol) are combined in methanol (30 mL) at ambient temperature and allowed to stir at room temperature overnight. Acetone (1 mL) is added, and mixture is evaporated under vacuum. The residue is partitioned between methylene chloride and water, and the water layer is extracted with methylene chloride twice more. The combined organic extracts are dried over anhydrous sodium sulfate, filtered, and evaporated under vacuum to give the title product as a colorless oil (0.325 g, 99%).

$^1$H NMR (CDCl$_3$) δ7.01 (d, 1H, J=3.3 Hz), 6.92 (m, 2H), 6.73 (d, 1H, J=8.3 Hz), 6.26 (d, 1H, J=3.6 Hz), 5.30 (s, 1H), 4.08 (d, 1H, J=7.2 Hz), 3.86 (t, 1H, J=7.2 Hz), 3.84 (d, 1H, J=7.2 Hz), 3.04 (s, 6H), 2.20 (s, 3H), 2.04 (m, 4H), 1.03 (s, 9H), 0.72 (t, 6H, J=7.0 Hz).

ES/MS: 416.2 (M+1).

Example 3 and Example 4

Preparation of Enantiomers 3'-[4-(2-hydroxy-3,3-dimethylbutoxy)-3-methylphenyl]-3'-[5-dimethylaminocarbonyl-2-furanyl]pentane

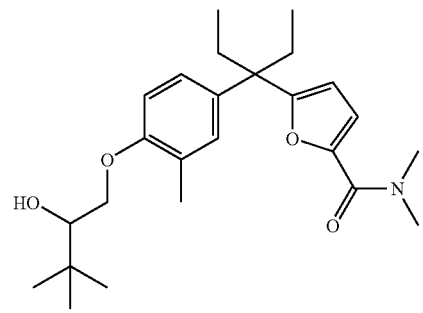

A mixture of racemic 3'-[4-(2-hydroxy-3,3-dimethylbutoxy)-3-methylphenyl]-3'-[5-dimethylaminocarbonyl-2-furanyl]pentane, Example 2 (300 mg), is chromatographed on a ChiralPak AD column with 40:60 IPA/hexane to give enantiomer 1, Example 3 (110 mg, 37%) and enantiomer 2, Example 4 (110 mg, 37%).

Enantiomer 1, Example 3

HPLC: ChiralPak AD (4.6×250 mm); 0.1% TFA/40% IPA/60% heptane; 1 ml/m (flow rate); Rt=5.6 m NMR eq. To Example 2.
Enantiomer 2, Example 4
HPLC: ChiralPak AD (4.6×250 mm); 0.1% TFA/40% IPA/60% heptane; 1 ml/m (flow rate); Rt=8.6 m Example 5

Preparation of 3'-[4-(2-oxo-3,3-dimethylbutoxy)-3-(2-butyl)phenyl]-3'-[5-dimethylaminocarbonyl-furan-2-yl]pentane

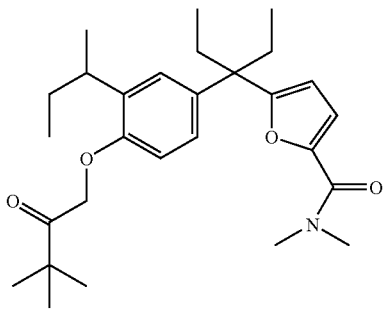

A. 3-(2-Furanyl)pentan-3-ol

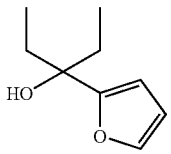

2-methyl furate (10.0 g, 79 mmol) is dissolved in THF (100 mL) under a nitrogen atmosphere. Ethyl magnesium bromide (3.0 M in $Et_2O$, 55 ml, 166 mmol) is added initially at room temperature. The reaction is cooled to −30° C., and the remaining ethyl Grignard added. The mixture is stirred overnight at room temperature. Saturated sodium bicarbonate solution (10 mL) is added to the stirring solution followed by diethyl ether (100 mL) and water (50 mL). The organic layer is separated and washed with water. The ether layer is dried over magnesium sulfate, filtered, and evaporated under vacuum to give 10.7 g of a oil, which was used without further purification.
$^1$H NMR ($CDCl_3$) δ 7.37 (s, 1H), 6.31 (d, 1H), 6.18 (d, 1H), 1.83 (m, 4H), 0.88 (t, 6H).

B. 3-(5-Carboxy-2-furanyl)pentan-3-ol

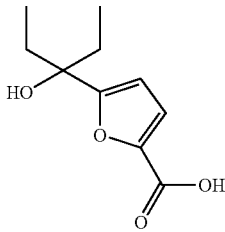

3-(2-Furanyl)pentan-3-ol (3.0 g, 19 mmol) is added to THF (20 mL) under a nitrogen atmosphere. The solution is stirred and cooled to −78° C. Sec-BuLi (1.3 M in cyclohexane, 31 mL, 41 mmol) is added dropwise maintaining the temperature below −55° C. After complete addition, the ice bath is removed and the solution slowly warmed to room temperature where it is stirred for 18 hours. The mixture is cooled to 48° C. and $CO_2$ gas is bubbled through the solution. A thick yellow past results and the temperature is increased to −10° C. Water (50 mL) is added and the solution is stirred at room temperature for 30 minutes. Ethyl acetate is added followed by water and the ph is adjusted to 1 with 1 N HCl. The organic layer is separated and the water layer was discarded. The organic layer is added to 1N NaOH solution and extracted. The pH of the water layer is adjusted to 1 with 1N HCl followed by addition of EtOAc. The organic layer is separated, dried over sodium sulfate, filtered, and evaporated under vacuum to give 2.7 grams of an oil.
$^1$H NMR ($CDCl_3$) δ8.5-10.0 (br,1H), 7.22 (d, 1H), 6.40 (d, 1H), 1.88 (m, 5H), 1.80 (t, 6H).

C. Z/E-3-(5-Methoxycarbonyl-2-furanyl)pent-2-ene

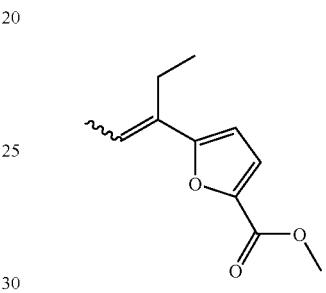

3-(5-Carboxy-2-furanyl)pentan-3-ol (200 mg, 1.1 mmol) is dissolved in methanol (20 mL). HCl (g) is bubbled through the solution for 30 seconds. The reaction is stirred for 20 minutes at room temperature with no reaction. The solution is heated to 60° C. for 2 hours. The solution is concentrated and water is added followed by solid $NaHCO_3$ until the pH was basic. Ethyl acetate is added and the solution is extracted. The organic layer is washed with water, dried over $MgSO_4$ and filtered. The filtrate is concentrated to 213 mg of an orange oil which is used as is.
$^1$H NMR ($CDCl_3$) δ 6.35 (q, 0.95H, J=6.8 Hz, E-isomer), 5.72 (q, 0.05H, J=6.8 Hz, Z-isomer). Irradiation of major isomer methyl doublet (1.83 ppm) produced a significant nuclear Overhauser effect upon the methylene quartet of the major isomer (2.40 ppm) as well as the vinyl H of the major isomer (6.35 ppm) confirming the major isomer as E.

D. 3'-[4-Hydroxy-3-(2-butyl)phenyl]-3'-[5-methoxycarbonyl-furan-2-yl]pentane

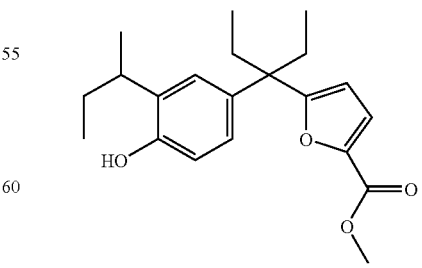

To Z/E-3-(5-methoxycarbonyl-2-furanyl)pent-2-ene (0.97 g, 5 mmol) in 2-(2-butyl)phenol (3.75 g, 25 mmol) is added boron trifluoride etherate (213 mg, 1.5 mmol) in methylene chloride (0.5 mL), and the mixture is stirred for 9 d at room temperature. The mixture is partitioned between diethyl ether and water, and the organic phase is washed twice more with water, once with satd brine, and dried over anhydrous sodium sulfate. The solvent is evaporated under vacuum, and the residue is chromatographed on 12 g of silica gel with a step gradient from 4% ethylacetate in hexanes to 6% ethylacetate in hexanes to give the title compound (1.12 g, 65%).

$^1$H NMR (CDCl$_3$) δ 7.10 (d, 1H, J=3.6 Hz), 6.93 (s, 1H), 6.82 (d, 1H, J=8.4 Hz), 6.22 (d, 1H, J=3.6 Hz), 4.56 (s, 1H), 3.82 (s, 3H), 2.91 (m, 1H), 1.97-2.19 (m, 4H), 1.59 (m, 2H), 1.19 (d, 3H, J=6.8 Hz), 0.82 (t, 3H, J=7.2 Hz), 0.69 (t, 6H, J=7.4 Hz).

ES/MS: 345.3 (M+1), 343.3 (M−1).

E. 3'-[4-Hydroxy-3-(2-butyl)phenyl]-3'-[5-carboxyl-furan-2-yl]pentane

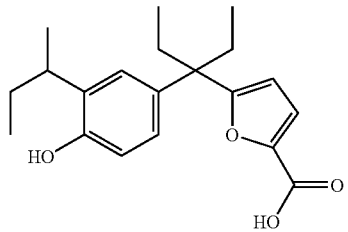

To 3'-[4-hydroxy-3-(2-butyl)phenyl]-3'-[5-methoxycarbonyl-furan-2-yl]pentane (0.2 g, 0.6 mmol) in methanol (5 mL) is added 5N NaOH (232 UL, 11.2 mmol), and the mixture is heated at 70° C. for 1.5 h in an open flask. Water is intermittently added to replace the evaporated methanol. The mixture is cooled to rt, and made acidic to pH paper with 5 N HCl. The product is extracted into methylene chloride, dried over anhydrous sodium sulfate, and evaporated to give the title compound (0.165 g, 87%).

$^1$H NMR (CDCl$_3$) δ 6.93 (d, 1H, J=2.4 Hz), 6.82 (d, 1H, J=8.4 Hz), 6.64 (d, 1H, J=8.4 Hz), 6.26 (d, 1H, J=3.6 Hz), 4.56 (s, 1H), 2.91 (m, 1H), 1.97-2.19 (m, 4H), 1.59 (m, 2H), 1.18 (d, 3H, J=6.8 Hz), 0.82 (t, 3H, J=7.2 Hz), 0.69 (t, 6H, J=7.2 Hz).

Exact mass: 331.192, calcd. 331.1909 for C20H27O4.

F. 3'-[4-Hydroxy-3-(2-butyl)phenyl]-3'-[5-dimethylaminocarbonyl-furan-2-yl]pentane

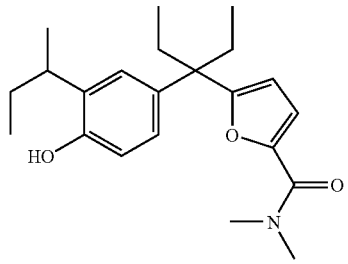

To 3'-[4-hydroxy-3-(2-butyl)phenyl]-3'-[5-carboxyl-furan-2-yl]pentane (0.164 g, 0.5 mmol) in DMF (0.5 mL) is added EDCI (120 mg, 0.6 mmol), 0.5 M HOAt in DMF (1.24 mL, 0.6 mmol), triethylamine (250 mg, 2.5 mmol), and dimethylamine hydrochloride (50 mg, 0.6 mmol). The mixture is stirred at rt for 64 h and partitioned between methylene chloride and satd sodium bicarbonate. The organic layer is dried over anhydrous sodium sulfate and evaporated. The residue is chromatographed on 4 g of silica gel with a step gradient from 20% ethylacetate in hexanes to 25% ethylacetate in hexanes to give the title compound (80 mg, 45%).

$^1$H NMR (400 mHz, CDCl$_3$) δ 7.01 (d, 1H, J=3.6 Hz), 6.92 (s, 1H), 6.79 (d, 1H, J=8.4 Hz), 6.63 (d, 1H, J=8.4 Hz), 6.24 (d, 1H, J=3.6 Hz), 4.91 (s, 1H), 3.03 (s, 6H), 2.92 (m, 1H), 1.97-2.05 (m, 4H), 1.52-1.63 (m, 2H), 1.18 (d, 3H, J=7.2 Hz), 0.82 (t, 3H, J=7.2 Hz), 0.70 (t, 6H, J=7.2 Hz).

LC/MS: 358.3 (M+1), 356.3 (M−1).

G. 3'-[4-(2-Oxo-3,3-dimethylbutoxy)-3-(2-butyl)phenyl]-3'-[5-dimethylaminocarbonyl-furan-2-yl]pentane Using a procedure analogous to Example 1D, 3'-[4-hydroxy-3-(2-butyl)phenyl]-3'-[5-dimethylaminocarbonyl-furan-2-yl]pentane (80 mg, 0.22 mmol) is reacted with 1-chloropinacolone to give the title compound as an oil (90 mg, 90%). to give the title compound (80 mg, 45%).

$^1$H NMR (400 mHz, CDCl$_3$) δ 7.01 (d, J=3.6 Hz, 1H), 6.97 (s, 1H), 6.84 (d, J=8.4 Hz, 1H), 6.25 (d, J=3.6 Hz, 1H), 4.82 (s, 2H), 3.03 (s, 6H), 3.14 (m, 1H), 1.98-2.12 (m, 4H), 1.48-1.64 (m, 2H), 1.25 (s, 9H), 1.17 (d, J=7.2 Hz, 3H), 0.81 (t, J=7.2 Hz, 3H), 0.70 (t, J=7.2 Hz, 6H).

ES/MS: 456.3 (M+1).

In procedures analogous to those above, the following examples are prepared:

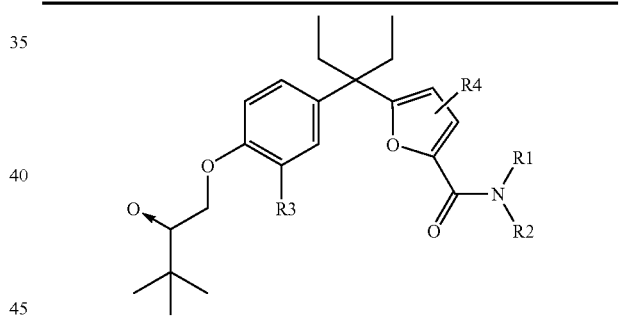

| Example No. | Oxo/Carbinol Rac/isomer | R1 | R2 | R3 | R4 |
|---|---|---|---|---|---|
| 6 | Oxo | Ethyl | H | Methyl | H |
| 7 | Oxo | Ethyl | Ethyl | Methyl | H |
| 8 | Oxo | Methyl | Methyl | Methyl | 4-methyl |
| 9 | Racemate | Methyl | Ethyl | Methyl | H |
| 10 | Isomer 1 | Methyl | Methyl | Ethyl | H |
| 11 | Isomer 2 | Methyl | Methyl | Ethyl | H |
| 12 | Isomer 1 | Methyl | Methyl | n-propyl | H |
| 13 | Isomer 1 | Methyl | Methoxy | Ethyl | H |

| Example | Name | Physical Data |
|---|---|---|
| 6 | 3'-[4-(2-oxo-3,3-dimethylbutoxy)-3-methylphenyl]-3'-[5-ethylaminocarbonyl-2-furanyl]-pentane | $^1$H NMR(300 mHz, DMSO-d$_6$) δ 8.09(m, 1H), 6.98(d, J=3.2Hz, 1H), 6.94(s, 1H), 6.86(d, J=8.4Hz, 1H), 6.62(d, |

| Example | Name | Physical Data |
|---|---|---|
| | | J=8.4Hz, 1H), 6.40(d, J=3.2Hz, 1H), 5.09(s, 2H), 3.19(m, 2H), 2.18(s, 3H), 1.95-2.10(m, 4H), 1.18(s, 9H), 1.03(t, J=7.0Hz, 3H), 0.60(t, J=7.0Hz, 6H). ES/MS: 414.3(M+1). |
| 7 | 3'-[4-(2-oxo-3,3-dimethyl-butoxy)-3-methylphenyl]-3'-[5-diethylaminocarbonyl-2-furanyl]-pentane | $^1$H NMR(CDCl$_3$) δ 7.00(d, J=3.2Hz, 1H), 6.90(s, 1H), 6.88(d, J=8.4Hz, 1H), 6.49(d, J=8.4Hz, 1H), 6.26(d, J=3.2Hz, 1H), 4.83(s, 2H), 3.37(m, 4H), 2.24(s, 3H), 1.95-2.10(m, 4H), 1.24(s, 9H), 1.15(m, 3H), 1.95(m, 3H), 0.68(t, J=7.2Hz, 6H). Exact Mass: calcd for C$_{27}$H$_{40}$NO$_4$(M+1) 442.2957, found 442.2950. |
| 8 | 3'-[4-(2-oxo-3,3-dimethyl-butoxy)-3-methylphenyl]-3'-[5-dimethylaminocarbonyl-3-methyl-2-furanyl]-pentane | $^1$H NMR(300mHz, CDCl$_3$) δ 6.95(s, 1H), 6.90(d, J=9.0Hz, 1H), 6.52(d, J=9.0Hz, 1H), 6.13(s, 1H), 4.85(s, 2H), 2.98(s, 6H), 2.50(s, 3H), 2.46(s, 3H), 1.95-2.12(m, 4H), 1.27(s, 9H), 0.70(t, J=7.2Hz, 6H). ES/MS: 428.4(M+1). |
| 9 | 3'-[4-(2-hydroxy-3,3-dimethyl-butoxy)-3-methylphenyl]-3'-[5-N-ethyl-N-methylamino-carbonyl-2-furanyl]pentane | $^1$H NMR(CDCl$_3$) δ 7.00(d, J=3.2Hz, 1H), 6.92(d, J=8.4Hz, 1H), 6.90(s, 1H), 6.70(d, J=8.8Hz, 1H), 6.25(d, J=3.2Hz, 1H), 4.06(d, J=8.8Hz, 1H), 3.84(t, J=9.0Hz, 1H), 3.70(d, J=8.8Hz, 1H), 3.40(m, 2H), 2.98(m, 3H), 2.44(s, 1H), 2.18(s, 3H), 1.98-2.10(m, 4H), 1.10(m, 3H), 1.02(s, 9H), 0.68(t, J=7.2Hz, 6H). ES/MS: 430.2(M+1). |
| 10 | 3'-[4-(2-hydroxy-3,3-dimethyl-butoxy)-3-ethylphenyl]-3'-[5-dimethylaminocarbonyl-2-furanyl]pentane enantiomer 1 | $^1$H NMR(CDCl$_3$) δ 7.00(d, J=3.2Hz, 1H), 6.92(m, 2H), 6.71(d, J=8.8Hz, 1H), 6.25(d, J=3.2Hz, 1H), 4.08(d, J=8.8Hz, 1H), 3.85(t, J=8.8Hz, 1H), 3.70(d, J=8.8Hz, 1H), 3.04(s, 6H), 2.59(q, J=8.0Hz, 2H), 2.41(m, 1H), 1.98-2.13(m, 4H), 1.14(t, J=7.4Hz, 3H), 1.01(s, 9H), 0.70(t, J=7.4Hz, 6H). ES/MS: 430.2(M+1), 447.2(M+NH$_4$). |
| 11 | 3'-[4-(2-hydroxy-3,3-dimethyl-butoxy)-3-ethylphenyl]-3'-[5-dimethylaminocarbonyl-2-furanyl]pentane enantiomer 2 | $^1$H NMR(CDCl$_3$) δ 7.00(d, J=3.2Hz, 1H), 6.92(m, 2H), 6.71(d, J=8.8Hz, 1H), 6.25(d, J=3.2Hz, 1H), 4.08(d, J=8.8Hz, 1H), 3.85(t, J=8.8Hz, 1H), 3.70(d, J=8.8Hz, 1H), 3.04(s, 6H), 2.59(q, J=8.0Hz, 2H), 2.41(m, 1H), 1.98-2.13(m, 4H), 1.14(t, J=7.4Hz, 3H), 1.01(s, 9H), 0.70(t, J=7.4Hz, 6H). |
| 12 | 3'-[4-(2-hydroxy-3,3-dimethyl-butoxy)-3-n-propyl-phenyl]-3'-[5-dimethylaminocarbonyl-2-furanyl]pentane enantiomer 1 | $^1$H NMR(CDCl$_3$) δ 7.00(d, J=3.2Hz, 1H), 6.92(m, 2H), 6.72(d, J=8.8Hz, 1H), 6.25(d, J=3.2Hz, 1H), 4.08(d, J=8.8Hz, 1H), 3.85(t, J=8.8Hz, 1H), 3.70(d, J=8.8Hz, 1H), 3.02(s, 6H), 2.54(t, J=7.0Hz, 2H), 2.39(m, 1H), 1.98-2.13(m, 4H), 1.55(m, 2H), 1.12(m, 1H), 1.01(s, 9H), 0.88(t, J=7.0Hz, 3H), 0.70(t, J=7.2Hz, 6H). ES/MS: 443.3(M+1), 461.3(M+NH$_4$). |
| 13 | 3'-[4-(2-hydroxy-3,3-dimethyl-butoxy)-3-ethylphenyl]-3'-[5-N-methoxy-N-methylamino-carbonyl-2-furanyl]pentane enantiomer 1 | $^1$H NMR(CDCl$_3$) δ 7.09(d, J=3.2Hz, 1H), 6.96(s, 1H), 6.95(d, J=8.8Hz, 1H), 6.71(d, J=8.8Hz, 1H), 6.25(d, J=3.2Hz, 1H), 4.08(d, J=8.8Hz, 1H), 3.85(t, J=8.8Hz, 1H), 3.70(d, J=8.8Hz, 1H), 3.60(s, 3H), 3.26(s, 3H), 2.59(q, J=7.2Hz, 2H), 2.40(d, J=2.4Hz, 1H), 2.0-2.19(m, 4H), 1.14(t, J=7.0Hz, 3H), 1.01(s, 9H), 0.71(t, J=7.4Hz, 6H). ES/MS: 446.2(M+1). |

Example 14

Preparation of 3'-[4-(2-hydroxy-2-ethylbutoxy)-3-methylphenyl]-3'-[5-dimethylaminocarbonyl-2-furanyl]pentane

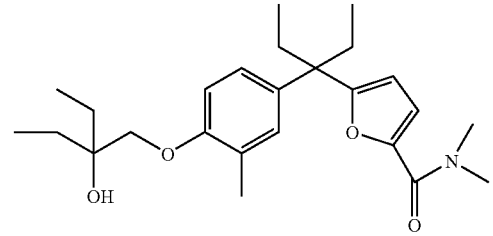

A. 3'-(4-Hydroxy-3-methyl-phenyl)-3'-pentanol

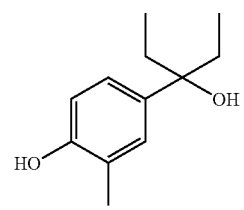

To methyl, 4-hydroxy-3-methylbenzoate (21.8 g, 0.13 mol) in 200 mL of THF is added 1.0 M ethylmagnesiuim bromide (433 mL, 0.43 mol) dropwise under nitrogen at ambient temperature. The mixture is stirred for 64 h and quenched with dilute sodium bicabonate. The mixture is triturated with diethyl ether five times (5×), and the combined organic layers are washed with dilute sodium bicarbonate, dried over anhydrous sodium sulfate, filtered, and evaporated under vacuum to give the title compound (27 g, 99%).

$^1$H NMR (400 mHz, CDCl$_3$) δ 7.29 (s, 1H), 7.04 (d, J=8.4 Hz, 1H), 5.72 (d, J=8.4 Hz, 1H), 4.74 (s, 1H), 3.75 (s, 1H), 2.26 (s, 3H), 1.82 (m, 4H), 0.76 (t, J=7.6 Hz, 6H).

ES/MS: 193.2 (M−1).

B. 3'(4-Methoxycarbonylmethoxy-3-methyl-phenyl)-3'-pentanol

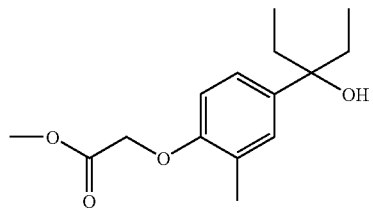

To 3'-(4-hydroxy-3-methyl-phenyl)-3'-pentanol (1.5 g, 7.7 mmol) in 20 mL of acetonitrile is added methyl, bromoacetate (0.73 mL, 7.7 mmol), potassium carbonate (4.26 g, 31 mmol) and catalytic potassium iodide (~0.1 g). the mixture is heated at 80° C. for 6 hr. The mixture is cooled and the solvent evaporated under vacuum. The residue is partitioned between diethylether and water. The organic layer is washed with water four times (4×), dried over anhydrous sodium sulfate, filtered, and evaporated under vacuum to give the title compound (2.06 g, 99%).

$^1$H NMR (400 mHz, CDCl$_3$) 7.14 (s, 1H), 7.11 (d, J=8.4 Hz, 1H), 6.64 (d, J=8.4 Hz, 1H), 4.64 (s, 2H), 3.80 (s, 3H), 2.30 (s, 3H), 1.80 (m, 4H), 0.76 (t, J=7.4 Hz, 6H).

C. 3'(4-Methoxycarbonylmethoxy-3-methyl-phenyl)-3'-(2-furanyl)pentane

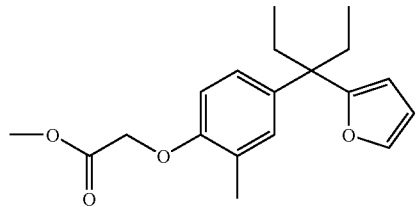

To 3'(4-methoxycarbonylmethoxy-3-methyl-phenyl)-3'-pentanol (2.0 g, 7.7 mmol) in furan (25 mL) is added boron-trifluoride etherate (0.39 mL, 0.3 mmol) at ambient temperature under nitrogen. The mixture is stirred for 4 hr, and quenched with satd. sodium bicarbonate. The product is extracted into diethylether, washed with water, satd. brine, dried over anhydrous sodium sulfate, filtered, and evaporated under vacuum. The residue is chromatographed on 40 g of silica gel with a gradient from 0-10% ethylacetate in hexanes to give a fraction containing the title compound (1.3 g, 53%).

$^1$H NMR (400 mHz, CDCl$_3$) 7.28 (s, 1H), 6.95 (s, 1H), 6.90 (d, J=8.0 Hz, 1H), 6.59 (d, J=8.0 Hz, 1H), 4.61 (s, 2H), 3.79 (s, 3H), 2.24 (s, 3H), 1.96-2.12 (m, 4H), 0.67 (t, J=7.4 Hz).

ES/MS: 317.1 (M+1).

D. 3'-[4-(2-Hydroxy-2-ethylbutoxy)-3-methylphenyl]-3'-[2-furanyl]pentane

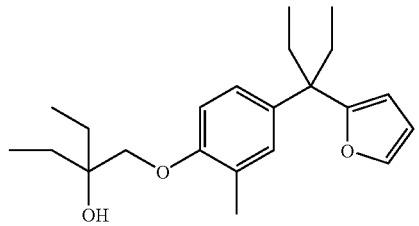

To 3'(4-methoxycarbonylmethoxy-3-methyl-phenyl)-3'-(2-furanyl)pentane (1.3 g, 4.1 mmol) in 10 mL of diethylether is added 1M ethylmagnesium bromide (10.2 mL, 10.2 mmol) dropwise, and the mixture is stirred over night. The mixture is quenched with sat sodium bicarbonate and triturated with diethylether five times (5×). The combined organic layers are washed with water, dried over anhydrous sodium sulfate, filtered, and evaporated under vacuum to give the title compound (1.33 g, 94%).

$^1$H NMR (400 mHz, CDCl$_3$) 7.29 (s, 1H), 6.93 (m, 2H), 6.72 (d, J=8.0 Hz), 6.29 (s, 1H), 6.18 (s, 1H), 3.79 (s, 2H), 2.20 (s, 3H), 1.16-2.12 (m, 4H), 1.66 (m, 4H), 0.93 (t, J=7.4 Hz, 6H), 0.67 (t, J=7.6 Hz, 6H).

ES/MS: 345.3 (M+1), 362.3 (M+NH4).

E. 3'-[4-(2-Hydroxy-2-ethylbutoxy)-3-methylphenyl]-3'-[5-carboxy-2-furanyl]pentane

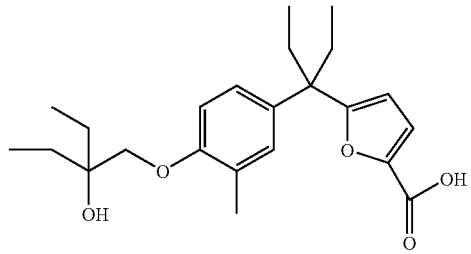

To 3'-[4-(2-hydroxy-2-ethylbutoxy)-3-methylphenyl]-3'-[2-furanyl]pentane (1.3 g, 3.8 mmol) in 10 mL cyclohexane and 2 mL diethylether at 0-5° C. under nitrogen is added 1.3 M sec-buthyllithium (6.5 mL, 8.5 mmol). After 5 min, excess carbon dioxide gas is bubbled in, and the mixture is stirred for 2 h. The mixture is partitioned between diethylether and water. The aqueous phase is made acidic with 6N HCl, and the product is extracted into diethylether. The ether layer is washed with water, dried over anhydrous sodium sulfate, filtered, and evaporated under vacuum to give the title compound (0.66 g, 44%) which is used as is.

ES/MS: 387.3 (M−1), 406.3 (M+NH4).

F. 3'-[4-(2-Hydroxy-2-ethylbutoxy)-3-methylphenyl]-3'-[5-dimethylaminocarbonyl-2-furanyl]pentane To 3'-[4-(2-hydroxy-2-ethylbutoxy)-3-methylphenyl]-3'-[5-carboxy-2-furanyl]pentane (0.66 g, 1.7 mmol) is added EDCI (0.38 g 2.0 mmol), 0.5 M HOAT in DMF (3.4 mL, 1.7 mmol), and 2M dimethylamine in THF (1.7 mL, 3.4 mmol) in DMF (2 mL). The mixture is stirred at room temperature for 2 h, and partitioned between diethylether and satd sodium bicarbonate. The organic layer is washed with water, satd brine, dried over anhydrous sodium sulfate, filtered, and evaporated under vacuum. The residue is chromatographed on 10 g of silica gel with a gradient from 5-30% ethylacetate in hexane to give a fraction containing the title compound (0.16 g, 23%).

$^1$H NMR (400 mHz, CDCl$_3$) 7.00 (d, J=3.6 Hz, 1H), 6.93 (d, J=8.2 Hz, 1H), 6.90 (s, 1H), 6.70 (d, J=8.2 Hz, 1H), 6.25 (d, J=3.6 Hz, 1H), 3.79 (s, 2H), 3.04 (s, 6H), 2.19 (s, 3H), 2.06 (m, 4H), 1.67 (m, 4H), 0.93 (t, J=7.4 Hz, 6H), 0.70 (t, J=7.4 Hz, 6H).

ES/MS: 416.3 (M+1), 433.3 (M+NH4).

TABLE 1

Summary of Experimental Results
(Compounds of the Invention)

| Test Cmpd.[1] | RXR-VDR heterodimer[2] EC$_{50}$ (nM) | VDR EC$_{50}$ (nM) (Caco-2 cells)[3] | OCN Promoter[4] EC$_{50}$ (nM) | Mouse Hypercal[5] μg/Kg/d |
|---|---|---|---|---|
| Ex. 1 | 3.3/0.6 | 191 | 5/3 | >1500 |
| Ex. 2 | | 25 | 3 | |
| Ex. 3 | 42/0.6 | 391 | 4.6/2.5 | >2000 |
| Ex. 4 | 10/0.5 | 333 | 2/1 | >2000 |
| Ex. 5 | 135/40 | 129 | 33/44 | |
| Ex. 6 | 320 | 315 | >1000 | |
| Ex 7 | | | 95 | >9000 |
| Ex. 8 | 156 | 758 | 125 | |
| Ex. 9 | 16 | 616 | 30 | |
| Ex. 10 | 13/0.1 | 191 | 1.6/0.5 | >1000 |
| Ex. 11 | 17.6 | 572 | 20 | >3000 |
| Ex. 12 | 188 | 187 | 0.5/0.1 | |
| Ex. 13 | 18 | 572 | 20 | >3000 |
| Ex 14 | 104 | 635 | 101 | |

TABLE 2

Summary of Experimental Results
(Compounds of the Invention)

| Test Cmpd.[1] | Kera. Prolif. IC$_{50}$ (nM) | IL-10. IC$_{50}$ (nM) |
|---|---|---|
| Ex. 1 | 15 | |
| Ex. 2 | | |
| Ex. 3 | 1 | |
| Ex. 4 | 4 | |
| Ex. 5 | 1000 | |
| Ex. 6 | 112 | |
| Ex 7 | 23 | |
| Ex. 8 | >1000 | |
| Ex. 9 | 28 | |
| Ex. 10 | 7 | |
| Ex. 11 | 18 | |
| Ex. 12 | 17 | |
| Ex. 13 | 18 | 4.6 |
| Ex 14 | 487/1000 | |

TABLE 3

Summary of Experimental Results
(Comparison Compounds)

| Test Cmpd.[1] | RXR-VDR (SaOS-2 cells)[2] EC$_{50}$ (nM) | VDR CTF (Caco-2 cells)[3] EC$_{50}$ (nM) | OCN Promoter[4] EC$_{50}$ (nM) | Mouse Hypercal[5] μg/Kg/d |
|---|---|---|---|---|
| AA | 5.02 | 16 | 5 | 0.06 |
| BB | 10.32 | 169.81 | 8.24 | >=20 |
| CC | 2427.7 | | >1000 | |
| DD | 109.44 | | 31.1 | 1000 |

TABLE 3-continued

Summary of Experimental Results
(Comparison Compounds)

| Test Cmpd.[1] | RXR-VDR (SaOS-2 cells)[2] EC$_{50}$ (nM) | VDR CTF (Caco-2 cells)[3] EC$_{50}$ (nM) | OCN Promoter[4] EC$_{50}$ (nM) | Mouse Hypercal[5] μg/Kg/d |
|---|---|---|---|---|
| EE | 429.99 | 891.16 | 341.25 | 1000 |
| FF | 3 | 57 | | |

TABLE 4

Summary of Experimental Results
(Comparison Compounds)

| Test Cmpd.[1] | Kera. Prolif. IC$_{50}$ (nM) | IL-10 IC$_{50}$ (nM) |
|---|---|---|
| AA | 120 | 1.2 |
| BB | 10 | 28 |
| CC | — | — |
| DD | 1060 | |
| EE | | |
| FF | 103 | 0.5 |

Explanation of Tables 1, 2, 3, and 4:

Test Compound numbers refer to the products of the corresponding Example Nos.

A slash mark "/" between numbers in a Table cell separates different experimental results obtained.

The control experiments are done with the double letter coded compounds identified as follows:

"AA"=1α,25-dihydroxyvitamin D$_3$

"BB"=3-(4-{1-Ethyl-1-[4-(2-hydroxy-3,3-dimethyl-butoxy)-3-methyl-phenyl]-propyl}-2-methyl-phenoxy)-propane-1,2-diol  "CC"=1-(4-{1-[4-(3,3-Dimethyl-2-oxo-butoxy)-3-methyl-phenyl]-cyclohexyl}-2-methyl-phenoxy)-3,3-dimethyl-butan-2-one "DD"=compound represented by the formula:

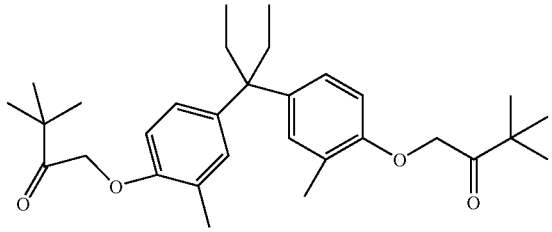

"EE"=compound represented by the formula:

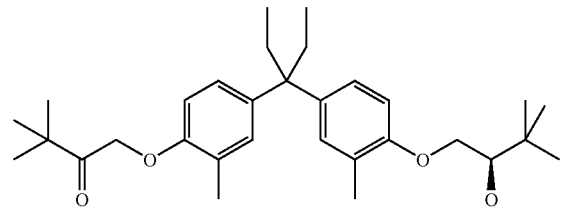

calcipotriol (structural formula below):

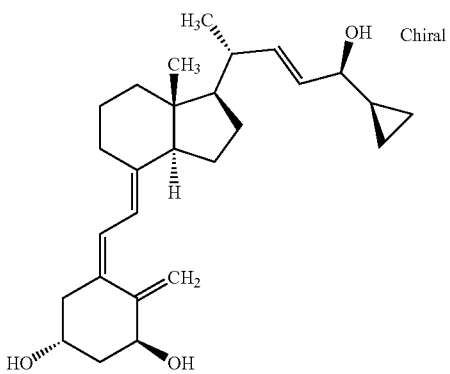

2. The RXR-VDR heterodimerization (SaOS-2 cells) test is described in the "Assay" section of the Description, infra.

3. The VDR CTF (Caco-2 cells) test is described in the "Assay" section of the Description, infra.

4. The OCN Promoter test is described in the "Assay" section of the Description, infra.

5. The Mouse Hypercalcemia test is described in the "Assay" section of the Description, infra.

6. The keratinocyte proliferation assay is described in the "Assay" section of the Description, infra.

7. The IL-10 induction assay is described in the "Assay" section of the Description, infra.

Assay Methods

Use of the Assay Methods:

The evaluation of the novel compounds of the invention for osteoporosis and other related diseases is done using a plurality of test results. The use of multiple assays is necessary since the combined properties of (i) high activity for the vitamin D receptor, and (ii) prevention of hypercalcemia must be achieved to have utility for the methods of treating diseases, which are also, aspects of this invention. Some of the tests described below are believed related to other tests and measure related properties of compounds. Consequently, a compound may be considered to have utility in the practice of the invention if is meets most, if not all, of the acceptance criteria for the above described tests.

The evaluation of the novel compounds of the invention for psoriasis is done using the Keratinocyte Proliferation Assay in combination with other assays that measure inhibition of IL-2 production and stimulation of IL-10 production in peripheral blood mononuclear cells (PBMCs).

Brief Description, Utility and Acceptance Criteria for the Assay Methods:

1. The RXR-VDR Heterodimer Assay:

This assay provides the VDR activity of a test compound. It is desirable to have low EC50 values for a compound in this assay. The lower the EC50 value, the more active the compound will be as a VDR agonist. Desired assay results are EC50 values less than or equal to 600 nM. Preferred assay results are less than 250 nM, and most preferably less than 150 nM.

2. The Caco-2 Cell Co-transfection Assay:

The Caco-2 cell assay is an indicator for the undesirable condition of hypercalcemia. This co-transfection assay is a surrogate assay for in vivo calcemic activity of VDR ligands. It is desirable to have high EC50 values for a test compound in this assay. The higher the EC50 values for a compound the less calcemic it will be in vivo. Desired assay results are EC50 greater than or equal to 300 nM. Preferred assay results are greater than 1000 nM.

3. The OCN (osteocalcin) Promoter Assay

The OCN Promoter Assay is an indicator and marker for osteoporosis. Desired assay results are EC50 less than or equal to 325 nM. Preferred assay results are less than 50 nM.

4. The Mouse Hypercalcemia Assay

The Mouse Hypercalcemia Assay is a six day hypercalcemia test for toxicity and selectivity. Acceptable test results are levels greater than 300 µg/kg/day. Preferred assay results are levels greater than 1000 µg/kg/day.

5. The Keratinocyte Proliferation Assay

This Assay is indicative for the treatment of psoriasis. An acceptable test result is IC50 value of less than or equal to 300 nM. Preferred assay results are IC50 values of less than 100 nM.

6. The IL-10 induction Assay

This is an in vitro efficacy assay for psoriasis, abscess and adhesion. Psoriasis involves both keratinocytes and immune cells. IL-10 is a unique cytokine because it is anti-inflammatory and immunosuppressive. This assay tells us whether a VDRM is able to function as an agonist in PBMCs (primary blood mononuclear cells) or not. A lower EC50 value is desirable in this assay since a compound with a lower EC50 value will be a better agonist in PBMCs. An acceptable test result is an EC50 value of less than 200 nM. Preferred assay results are EC50 values of less than 100 nM.

7. Other Compound Assay Standards

An alternative measure of the efficacy of compounds of the invention for treatment of osteoporosis is a numerical ratio calculated as follows:

Dose Threshold needed to induce hypercalcemia divided by

Dose Threshold needed for bone efficacy

An alternative measure of the efficacy of compounds of the invention for treatment of psoriasis is a numerical ratio calculated as follows:

Dose Threshold needed to induce hypercalcemia divided by

Dose Threshold needed to induce keratinocyte proliferation

For the above ratios, Dose Thresholds are determined from dose response curve data.

8. The CaT1 (calcium transporter 1) Assay

The CaT1 Assay is an indicator for the undesirable condition of hypercalcemia. The higher the EC50 values for a compound the less calcemic it will be in vivo. Desired assay results are EC50 greater than or equal to 500 nM. Preferred assay results are greater than 1000 nM.

Details of the Assay Methods (1) Materials and Method for RXR-VDR Heterodimerization Assay:
Transfection Method:
FuGENE 6 Transfection Reagent (Roche Cat #1 814 443)

Growth Media:
   D-MEM High Glucose (Gibco BRL Cat #11054-020), 10% FBS, 1% antibiotic-antimycotic (Ab-Am)
FBS heat inactivated (Gibco BRL Cat #10092-147)
Ab-Am (Gibco BRL Cat #15240-062)
   Cells:
   Grow SaOs-2 cells in T-152 cm$^2$ culture flasks in growth media.
   Keep the density at 5-6×10$^5$ cells/ml
   Passage cells 1:3 twice a week
   Add Trypsin EDTA (Gibco BRL Cat #25300-020)and incubate
   Resuspend cells in plating media and transfer into growth media.
   Wash Media:
   HBSS Low Glucose Without Phenol Red (Gibco BRL Cat #14175-095), 1% Ab-Am
   Plating Media:
   D-MEM Low Glucose Without Phenol Red (Gibco BRL Cat #11054-020), 1% Ab-Am D-MEM
Stripped FBS (Hyclone Cat#SH30068.03 Lot #AHM9371)
Ab-Am
   Transfection/Treatment Media:
   D-MEM Low Glucose Without Phenol Red only
   T-152 cm$^2$ culture flask:
   Use Corning Coastar T-152 cm$^2$ culture flask (Cat #430825) to grow the cells
   Flat well Plates:
   Use well plate to plate cells
   Use Deep well plate sterile to make up treatment media.
   Luciferase Assay Reagent:
   Use Steady-Glo Luciferase Reagent from Promega (Cat #E2550) Consists of:
      a. E2533 Assay Substrate, lyopholized product and
      b. E2543 Assay Buffer.
   Thaw at room temperature
   Store Day 1: Cell Plating:
Cell Harvesting
Aspirate media from culture flask, rinse cells with HBSS and aspirate.
Add trypsin and incubate.
When cells appear detached, resuspend cells in growth media.
Transfer into a new flask with fresh growth media for passaging the cells.
Plate well plates and two extra plates A. Cell Count
Mix the cell suspension using pipette
Use Hematocytometer to count the cells
Load cell suspension onto the hemocytometer chamber
Count cells.
   Plate seeding:
Use plating media 10% Stripped FBS in D-MEM Low Glucose, Without Phenol Red, 1% Ab-Am
Plate 14 plates @ 165 µl/well.
In sterile flask add cell suspension
to plating media.
Mix.
Add cells/well.
Place the cells in the incubator.
Cells should be about 75% confluent prior to transfection.

Day 2: Transfection
   Step 1: DNA and Media
   Add plain DMEM media to tubes for mixing the DNA
   Add the Reporter gene pFR-LUC
   Add the Gal-4-RXR-DEF and VP16-VDR-LBD
   Step 2: FuGENE and Media
   Prepare plain DMEM media in a ubes for mixing PuGENE
   Add FuGENE 6 Transection Reagent
   Incubate
   Step 3: FuGENE, DNA and Media Complex
   Add FuGENE Media complex from step 2 to DNA Media complex from step1
   Incubate
   Step 4: FuGENE, DNA and Media Complex to-well plate
   Add FuGENE-DNA-Media complex from step 3 to each plate
   Incubate.

Day 3: Dosing
Treatment preparation
Allow for transfection time
Make a stock solution of the compounds in DMSO
Vortex until all the compounds has been dissolved.
Further dilute in D-MEM (Low Glucose—With out Phenol Red)
Add compounds in quadruplicate to give final volume
Incubate.

Day 4: Luciferase Assay
Read the plates after drug treatment
Remove part of media from all the wells and leave remainder
Add Steady-Glo Luciferase Reagent mixture/wells
Incubate
Count each well using a Luminescence counter, Top Count NXT by Packard Set a delay between plates to reduce the background.

(2) Materials and Method for The Caco-2 Cell Assay:
   Caco-2 cells, grown in phenol red free, DMEM (Invitrogen, Carlsbad, Calif.) containing 10% charcoal-stripped FCS (Hyclone, Logan, Utah), were transfected with Fugene 6 reagent (Roche Diagnostics, Indianapolis, Ind.). Cells (5000/well) were plated 18 h before transfection in a 96 well plate. The Cells were transfected with Gal-4-responsive reporter pFRLuc (150 ng, Stratagene, La Jolla Calif.) and the receptor expression vector pGal-4-VDR-LBD (10 ng), along with Fugene 6 reagent (0.2 µl/well). The DNA-Fugene complex was formed by incubating the mixture for 30 min at room temperature. The cells were transfected in triplicate for 5 h, and treated with various concentrations of VDR ligands (form 0.01 nM to 10,000 nM concentration range) 18 h post-transfection. The luciferase activity was quantified using Steady-Glo reagent kit (Promega, Madison, Wis.) as per manufacturer's specifications.

(3) Materials and Method for The OCN Promoter Assay:
   The activation of osteocalcin by VDR ligands was evaluated in a rat osteoblast-like cell line RG-15 (ROS 17/2.8) stably expressing rat osteocalcin promoter fused with luciferase reporter gene. The stable cell lines were established as reported before (Activation of Osteocalcin Transcription involves interaction of protein kinase A- and Protein kinase C-dependent pathways. Boguslawski, G., Hale, L. V., Yu, X.-P., Miles, R. R., Onyia, J. E., Santerre R. F., Chandrasekhar, S. J. Biol. Chem. 275, 999-1006, 2000). Confluent RG-15 cells maintained in DMEM/F-12 medium (3:1) containing 5% FBS, 3001 µg/ml G418 and at 37° C. under 5% $CO_2$/95% air atmosphere were trypsinized (0.25% trypsin) and plated into white opaque 96-well cell culture plates (25000 cells/well). After 24 hr, cells (in DMEM/F-12 medium +2% FBS) were treated with various concentrations of compounds, dissolved in DMSO. The final DMSO concentration remained at 0.01% (v/v). After 48 hr treatment, the medium was removed, cells were lysed with 50 µl of lysis buffer (From Luciferase reporter assay system, Roche Diagnostics, Indianapolis, Ind.) and assayed for luciferase activity using the Luciferase Reporter Gene Assay kit from Boehringer Mannheim as per manufacturer's specifications.

(4) Materials and Method for The Mouse Hypercalcemia Assay:

Weanling, virus-antibody-free, five to six weeks old female DBF mice (Harlan, Indianapolis, Ind.) are used for all the studies. Animals are allowed to acclimate to local vivarium conditions for 2 days. Mice are maintained on a 12 hr light/dark cycle at 22° C. with ad lib access to food (TD 5001 with 1.2% Ca and 0.9% P, Teklad, Madison, Wis.) and water. The animals then are divided into groups with 4-5 mice per group. Different doses of test compounds prepared in 10% Ethanol and 90% sesame oil are administered to mice orally via gavage for 6 days. $1\alpha\text{-}25(OH)_2D_3$ 0.5 µg/kg/d was also given to one group of mice as the positive control. Serum ionized calcium is evaluated at 6 hours after the last dosing under isoflurane anesthesia by Ciba-Corning Ca++/PH Analyzer, (Model 634, Chiron Diagnostics Corp., East Walpole, Mass.). Raw data of group differences is assessed by analysis of variance (ANOVA) using Fisher's protected least significant difference (PLSD) where the significance level was $P<0.05$.

(5) The Keratinocyte Proliferation Assay:

KERtr cells (Human skin keratinocyte transformed with a retrovirus vector, obtained from ATCC) were plated in 96-well flat-bottomed plates (3000 cells/well) in 100 µl keratinocyte serum free medium supplemented with bovine pituitary extract in the absence of EGF (Life Technologies, Rockville, Md.) and incubated at 37° C. for two days. The cells were treated with various concentrations of VDR ligands (ten-fold serial dilution from 10,000 nM to 0.1 nM in triplicate), dissolved in 100 µl keratinocyte serum free medium supplemented with bovine pituitary extract in the absence of EGF and incubated at 37° C. for 72 hr. BrdU (5-bromo-2'-deoxyuridine) incorporation was analyzed as a measure of DNA replication (Cell proliferation ELISA kit, Roche Diagnostics, Indianapolis, Ind.) and absorbance was measured at 405 nm. Potency values ($IC_{50}$) values were determined as the concentration (nM) of compound that elicited a half-maximal response.

(6) Materials and Method for human IL-10 Induction Assay:
Isolation of peripheral blood mononuclear cells (PBMCs):
A. Collect 50 ml of human blood and dilute with media, RPMI-1640.
B. Prepare sterile tubes with ficol.
C. Add diluted blood to tubes.
D. Centrifuge.
E. Discard the top layer and collect the cells from middle layer.
F. Divide all cells into four tubes and add media.
G. Centrifuge.
H. Aspirate off media and resuspend.
I. Collect all cells
J. Centrifuge. at 1200 rpm for 10 minutes.
K. Resuspend in RPMI-1640 with 2% FBS and count cells
Stimulation of PBMC:
L. Prepare TPA in DMSO.
M. Dissolve PHA in water.
N. Plate TPA/PHA treated PBMCs in well plates.
O. Incubate.

Treatment:
P. Prepare all compound dilutions in plain RPMI-1640 media.
Q. Add diluted compound.
R. Incubate.
Sample Collection and assay:
S. Remove all the cells by centrifugation and assay the supernatant for IL-10 by immunoassay.
1) T. Perform IL-10 assay using anti-human IL-10 antibody coated beads, as described by the manufacturer (Linco Research Inc., St. Charles, Mo.).

(8) CaT1 assay

Human colon carcinoma, Caco-2 cells, maintained in DMEM (high glucose with mM Hepes buffer; Invitrogen, Carlsbad, Calif.) supplemented with 10% fetal bovine serum (Invitrogen, Carlsbad, Calif.), are plated at 5500 cell per well in a 96-well plate in a total volume of 100 µl/well. The cells are kept in the 96-well plate for 6 days to differentiate them to small intestinal cells that express the calcium transporter, CaT1. On day 3 after plating, old media is removed and replaced with fresh media (150 µl/well). On day 6 the old media is removed and the cells are kept in treatment media (180 µl/well) that contained 10% charcoal stripped fetal bovine serum (Hyclone, Logan, Utah) in DMEM (low glucose, without phenol red; Invitrogen, Carlsbad, Calif.). The cells are treated with various concentrations of VDR ligands (from 0.01 nM to 10,000 nM concentration range) prepared in treatment media (20 µl/well). Twenty hours post-treatment, total RNA is prepared by RNeasy 96 method as described by the manufacturer (Qiagen, Valencia, Calif.). The RNA is reverse transcribed and amplified for human CaT1 and GAPDH (control) messages by quantitative RT-PCR using ABI PRISM 7900HT Sequence Detection System according to manufacturer's instructions (Applied Biosystems, Foster City, Calif.). Optimized primer pairs and probes for human CaT1 and GAPDH genes are obtained commercially (Applied Biosystems, Foster City, Calif.). Each 20 µl quantitative RT-PCR reaction in a 384-well Taqman PCR plate consists of forward and reverse primers (900 nM), Taqman probe (200 nM), total RNA (4 µl form each well of the 96-well culture plate) and 10 µl of Taqman Universal PCR Master Mix (Roche Diagnostics, Indianapolis, Ind.). Reactions are incubated at 48° C. for 30 minutes, followed by 10 minutes at 95° C. and subjected to 40 cycles of PCR (95° C. for 15 seconds followed by 60° C. for 1 minute). GAPDH is used as an internal control and its primer and probe set are obtained commercially (Applied Biosystems, Foster City, Calif.).

We claim:

1. A compound represented by a formula below or a pharmaceutically acceptable salt derivative thereof:

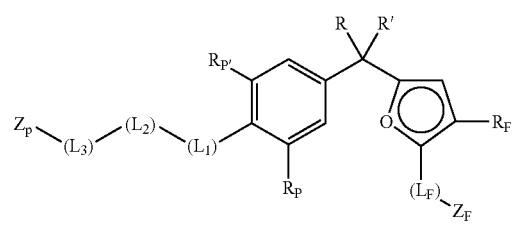

wherein;

R and R' are independently $C_1$-$C_4$ alkyl;

$R_P$, $R_{P'}$, and $R_F$ are independently selected from the group consisting of hydrogen and $C_1$-$C_4$ alkyl;

($L_1$) is oxygen;
($L_2$) is —C(R40)$_2$—, where each R40 is independently hydrogen, $C_1$-$C_5$ alkyl or $C_1$-$C_5$ fluoroalkyl;
($L_3$) is —C(=$X_1$)—, where $X_1$ is O, S, CH$_2$, or;
($L_F$) a bond;
$Z_F$ is

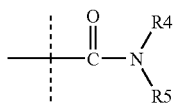

where R4 and R5 are independent hydrogen, $C_1$-$C_4$ alkyl, —O—$C_1$-$C_4$ alkyl, $C_2$-$C_4$ alkenyl, $C_2$-$C_4$ alkynyl, $C_1$-$C_4$ haloalkyl, —NH($C_1$-$C_4$ alkyl), or cyclopropyl, with the proviso that only one of R4 or R5 may be hydrogen;

$Z_P$ is
- methyl,
- ethyl,
- n-propyl,
- 1-methylethyl,
- 1-methylpropyl,
- 2-methylpropyl,
- 1,1-dimethylethyl,
- 1,1-dimethylpropyl,
- 1,2-dimethylpropyl, or
- 2,2-dimethylpropyl.

2. The compound of claim 1 wherein
$Z_P$ is 1,1-dimethylethyl, 1,2-dimethylpropyl, 2,2-dimethylpropyl;
$Z_F$ is selected from:
- —C(O)NHMe,
- —C(O)NHEt,
- —C(O)NHOMe,
- —C(O)NHOEt,
- —C(O)NH(iPr),
- —C(O)NH(tBu),
- —C(O)NH(CF$_3$),
- —C(O)N(Me)$_2$,
- —C(O)NMeEt,
- —C(O)NMe(iPr),
- —C(O)NMe(tBu),
- —C(O)NMe(CF$_3$),
- —C(O)N(Et)$_2$, or
- —C(O)NEt(iPr);

or a pharmaceutically acceptable salt thereof.

3. The compound of claim 2 wherein
$Z_F$ is selected from:
- —C(O)NHMe,
- —C(O)NHEt,
- —C(O)NH(iPr),
- —C(O)NH(tBu),
- —C(O)N(Me)$_2$,
- —C(O)NMeEt,
- —C(O)NMe(iPr),
- —C(O)NMe(tBu),
- —C(O)N(Et)$_2$, or
- —C(O)NEt(iPr);

or a pharmaceutically acceptable salt thereof.

4. A compound according to claim 1, or a pharmaceutically acceptable salt thereof, represented by formulae A to J as follows:

A)
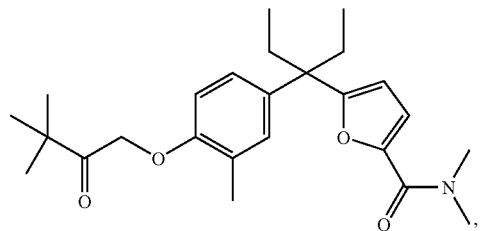

B)
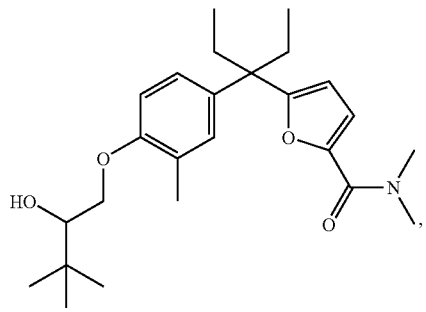

C)
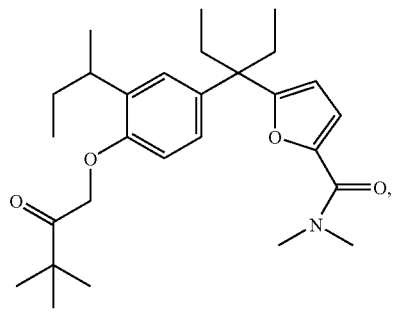

E)
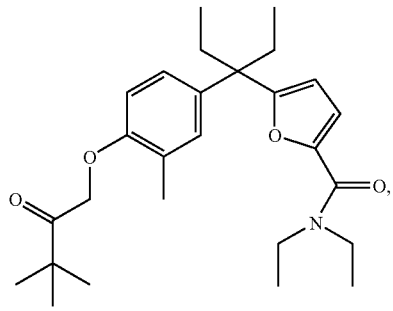

F)
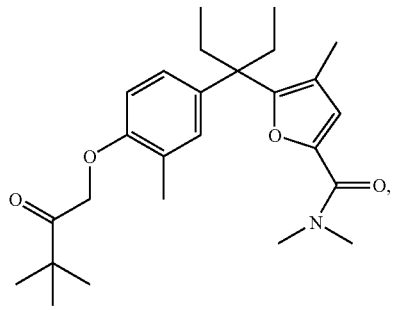

G) 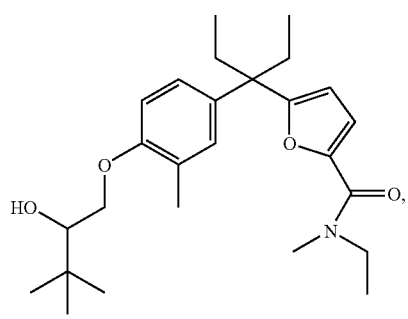

H) 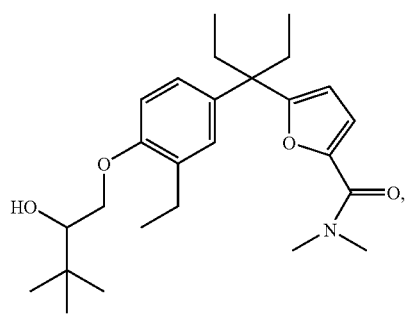

I) 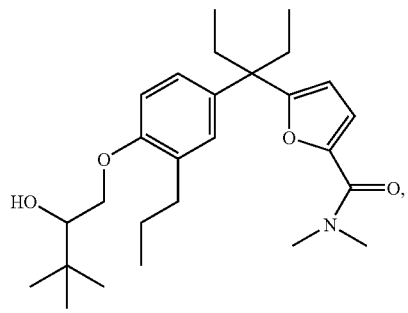

J) 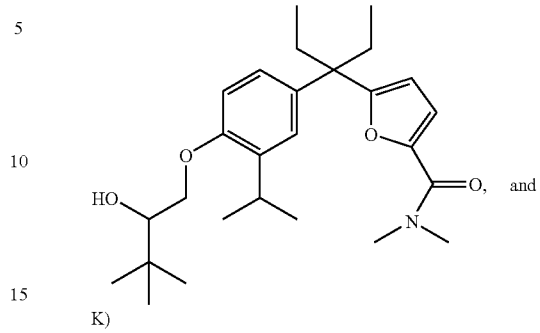

K) 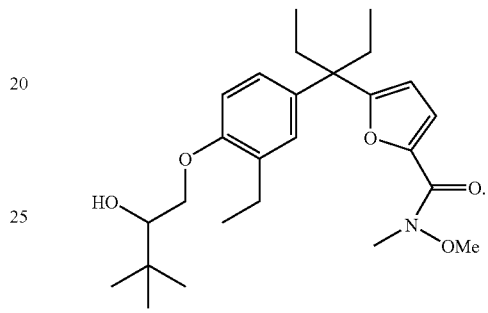

5. A pharmaceutical formulation comprising the compound of claim 1 together with a pharmaceutically acceptable carrier or diluent.

6. A method of treating a mammal to alleviate the pathological effects of Osteoporosis or Psoriasis wherein the method comprises administering a pharmaceutically effective amount of at least one compound of claim 1.

7. The method of claim 6 for the treatment of psoriasis.

8. The method of claim 6 for the treatment of osteoporosis.

9. The method of treating disease states mediated by the Vitamin D receptor, wherein a mammal in need thereof is administered a pharmaceutically effective amount of a compound of claim 1.

* * * * *